(12) United States Patent
Hashish et al.

(10) Patent No.: US 8,187,056 B2
(45) Date of Patent: May 29, 2012

(54) PROCESS AND APPARATUS FOR SURFACE-FINISHING

(75) Inventors: Mohamed Hashish, Bellevue, WA (US);
Paul Tacheron, Auburn, WA (US);
Steven J. Craigen, Auburn, WA (US);
Bruce M. Schuman, Kent, WA (US)

(73) Assignee: Flow International Corporation, Kent, WA (US)

( * ) Notice: Subject to any disclaimer, the term of this patent is extended or adjusted under 35 U.S.C. 154(b) by 1335 days.

(21) Appl. No.: 11/640,143

(22) Filed: Dec. 14, 2006

(65) Prior Publication Data

US 2008/0142050 A1   Jun. 19, 2008

(51) Int. Cl.
*B24B 1/00* (2006.01)

(52) U.S. Cl. ............ 451/38; 451/49; 451/51; 451/57; 451/60; 451/61

(58) Field of Classification Search ............. 83/53, 177; 134/8, 22.12, 22.18, 23, 24, 36, 37, 54, 152; 134/166 R, 167 R, 169 C; 623/38, 39, 40, 623/49, 51, 57, 61, 87; 451/60
See application file for complete search history.

(56) References Cited

U.S. PATENT DOCUMENTS

| | | | | | |
|---|---|---|---|---|---|
| 1,952,848 | A | * | 3/1934 | Eckler | 451/38 |
| 2,719,387 | A | | 10/1955 | Fahrney | |
| 3,427,763 | A | * | 2/1969 | Maasberg et al. | 451/40 |
| 4,712,332 | A | * | 12/1987 | Smith | 451/5 |
| 5,242,399 | A | * | 9/1993 | Lau et al. | 604/104 |
| 5,364,474 | A | * | 11/1994 | Williford, Jr. | 134/32 |
| 5,512,318 | A | | 4/1996 | Raghavan et al. | 427/230 |
| 5,522,882 | A | * | 6/1996 | Gaterud et al. | 623/1.11 |
| 5,603,721 | A | * | 2/1997 | Lau et al. | 606/195 |
| 5,643,058 | A | | 7/1997 | Erichsen et al. | 451/99 |
| 5,788,558 | A | * | 8/1998 | Klein | 451/36 |
| 5,885,133 | A | * | 3/1999 | Williams, Jr. | 451/40 |
| 6,000,308 | A | | 12/1999 | LaFountain et al. | 83/53 |
| 6,012,975 | A | * | 1/2000 | Jager | 451/87 |
| 6,019,298 | A | | 2/2000 | Raghavan et al. | 239/599 |
| 6,045,623 | A | * | 4/2000 | Cannon | 134/8 |
| 6,106,373 | A | * | 8/2000 | Fabris | 451/57 |
| 6,183,353 | B1 | | 2/2001 | Frantzen | 451/104 |
| 6,244,934 | B1 | * | 6/2001 | Miyai et al. | 451/38 |
| 6,280,302 | B1 | | 8/2001 | Hashish et al. | 451/102 |
| 6,920,662 | B2 | * | 7/2005 | Moore | 15/104.2 |
| 6,981,906 | B2 | | 1/2006 | Hashish et al. | 451/2 |
| 7,249,606 | B2 | * | 7/2007 | McCleary et al. | 134/104.1 |
| 7,459,028 | B2 | * | 12/2008 | Kral et al. | 134/7 |
| 7,637,800 | B2 | * | 12/2009 | Hamann et al. | 451/36 |
| 2003/0106218 | A1 | * | 6/2003 | Jalisi et al. | 29/896.6 |

OTHER PUBLICATIONS

Summers, "Waterjet Use in Decontaminating Surfaces," 1-7.
Clanet et al., "Depth of penetration of bubbles entrained by a plunging water jet," *Phys. Fluids* 9(7):1864-1866, Jul. 1997.

(Continued)

*Primary Examiner* — Timothy V Eley
(74) *Attorney, Agent, or Firm* — Seed IP Law Group PLLC

(57) ABSTRACT

A processing apparatus is provided to surface-finish or otherwise process features of a workpiece, such as a lumen of a stent. The fluid jet apparatus can have a nozzle system and a holder for holding and positioning the workpiece with respect to the nozzle system. A fluid jet outputted from the nozzle system is used to form a desired surface-finish.

27 Claims, 14 Drawing Sheets

OTHER PUBLICATIONS

Dibra et al., "Influence of Stent Surface Topography on the Outcomes of Patients Undergoing Coronary Stenting: A Randomized Double-Blind Controlled Trial," *Catherization and Cardiovascular Interventions* 65:374-380, 2005.

Wenaweser, "Stent Thrombosis is Associated with an Impaired Response to Antiplatelet Therapy," URL=http://www.cardiosource.com/expertopinions/hottopics/article.asp?paperID=198, download date Oct. 26, 2006.

* cited by examiner

PROCESS AND APPARATUS FOR SURFACE-FINISHING

BACKGROUND OF THE INVENTION

1. Field of the Invention

The present invention relates generally to processes and apparatuses for finishing workpieces, and in particular, processes and apparatuses for surface-finishing.

2. Description of the Related Art

Tubular members often have surfaces that require surface-finishing. Tubular members are used to form luminal prostheses that have lumens defining fluid pathways. Stents are one type of luminal prosthesis that can be placed in various types of body vessels, such as body vessels of the vasculature system (e.g., blood vessels), respiratory system, and gastrointestinal system. Arterial stents, for example, can support dissections in arterial tissue that may occur during medical procedures, such as balloon angioplasty procedures intended to maintain fluid pathways. To support weakened or damaged blood vessels, stents may be used to form stent grafts, which are in turn used to support the blood vessels.

A stent with a lattice structure can serve as a scaffold for engaging a body vessel to maintain vessel patency. The lattice structure of an expandable stent provides for expansion from a collapsed configuration for delivery to an expanded configuration for implantation. The lattice structure can be formed by a plurality of struts, beams, or ribs often made of stainless steel, nickel titanium alloy, and other biocompatible materials.

Various types of fabrication processes are used to form the lattice structure that provides the desired functionality. However, these fabrication processes can result in contamination (e.g., buildup of foreign matter) and in the formation of an unwanted stent topography, which may include relatively rough or sharp edges, hanging burrs, or other surface irregularities. After forming the lattice structure, the stent may therefore require further processing to obtain a desired surface-finish. Mechanical machining is one type of fabrication process that often leads to the formation of outwardly extending burrs (e.g., burrs extending either radially inward or outward). Laser cutting processes often produce stents with rough surfaces along cutouts as well as an appreciable amount of unwanted material, such as slag particles. Other conventional cutting techniques used to form complicated lattice structures tend to suffer from similar problems.

Surface-finishing processes are performed to obtain the desired surface topography (e.g., surface smoothness) to improve the stent's performance when implanted in a subject. Rough edges or protuberances of an arterial stent, for example, may facilitate the formation of thrombus and ultimately lead to closing of the stent's lumen, clot formation, damage to arterial walls, stenosis, and other undesirable conditions. Unfortunately, additional medical procedures may need to be performed to, for example, further expand the stent, remove unwanted accumulated material, replace the stent, or combat stenosis.

The stent's topology may also be unsuitable for many delivery techniques. Balloon expandable stents are often deployed using a controllably inflatable balloon (e.g., an angioplasty balloon) made from a thin material suitable for containing a pressurized inflation fluid, such as saline. Unfortunately, uneven surfaces, rough or sharp edges, burrs, debris, or similar structures may puncture and rupture the balloon when the balloon is inflated outwardly against the sidewall of the stent. Accordingly, these types of destructive features on the stent have to be removed before expanding the stent.

Mechanical surface-finishers, such as rough files, are often used to perform surface-finishing processes. To remove inwardly extending burrs, a rough file is inserted into the lumen of the stent and used to break off or wear down the burrs. Because stents have relatively narrow lumens, it is often difficult to insert such files into the lumens, let alone to manipulate the files to produce the desired surface-finish. Additionally, large burrs may block the lumens and thus make it difficult to insert and advance the files through the lumens. Even if a file can be inserted into a stent's lumen, the file can damage or break the stent's sidewall during surface-finishing, especially if the sidewall is relatively thin.

Chemical surface-finishing is also unsuitable for producing a desired topography because it removes material from all the exposed surfaces of the stent. For example, if a chemical surface-finisher is employed to remove large burrs, it may remove significant amounts of material from all the surfaces to which it is exposed, thus significantly altering the overall geometry of the stent. It is also difficult to control the uniformity of the stent's geometry when utilizing chemical surface-finishers.

The present disclosure is directed to overcome one or more of the shortcomings set forth above, and provide further related advantages.

BRIEF SUMMARY OF THE INVENTION

Some embodiments disclosed herein include the realization that a fluid jet apparatus can be used to surface-finish various surfaces and relatively small features of a workpiece, such as an outer or inner surface of a tubular member. The fluid jet apparatus can have a nozzle system and a holder for holding and positioning the workpiece with respect to the nozzle system. To produce a generally uniform surface-finish, the holder can rotate the workpiece while a fluid jet emitted from the nozzle system removes material from the workpiece's periphery.

The workpiece in some embodiments is a tubular member with a deep hole or through hole. The holder can rotate the tubular member about the fluid jet flowing through a passageway of the tubular member. The fluid jet can be concentrically or eccentrically positioned with respect to the tubular member, and can be generally parallel or oblique to an axis of rotation about which the tubular member rotates.

In some embodiments, a method of processing a tubular workpiece is provided. The method includes positioning a tubular workpiece in a holder. The workpiece has an inner surface defining a central lumen. A fluid jet is delivered through the central lumen of the tubular workpiece in a first direction relative to the central lumen while the tubular workpiece is in the holder. The fluid jet is delivered through the central lumen of the tubular workpiece for a selected period of time such that the fluid jet removes a desired amount of material from the workpiece.

In other embodiments, a method of processing a tubular workpiece having an inner surface and an outer surface is provided. The inner surface of the workpiece defines a lumen. The method includes positioning a mandrel through the lumen of the tubular workpiece. The mandrel defines an axis of rotation. A fluid jet contacts a first section of the outer surface of the tubular workpiece. The tubular workpiece is rotated about the axis of rotation with the mandrel such that the fluid jet is delivered against a second section of the outer surface.

In some embodiments, an apparatus for processing a tubular workpiece with a lumen includes a fluid jet delivery system capable of producing a fluid jet for processing the workpiece and a rotatable workpiece holder. The rotatable workpiece holder is positioned with respect to the fluid jet delivery system such that the rotatable workpiece holder may rotate the tubular workpiece about an axis of rotation while the fluid jet delivered from the fluid jet delivery system contacts the tubular workpiece.

In other embodiments, an apparatus for processing a tubular workpiece with a lumen is provided. The apparatus comprises a fluid jet delivery system and a workpiece holder. The fluid jet delivery system is capable of producing a fluid jet for processing the workpiece. The workpiece holder is positioned with respect to the fluid jet delivery system such that most of the fluid jet from the fluid jet delivery system flows into the lumen of the workpiece. The lumen has an average diameter of less than about 0.6 inches. In some embodiments, the lumen has an axial length less than about 2 inches and the average diameter is less than about 0.4 inch.

In yet other embodiments, an apparatus for processing a tubular workpiece with a lumen is provided. The apparatus includes a workpiece holder for rotatably holding a tubular workpiece and a nozzle system. The nozzle system is configured to produce a fluid jet for processing the workpiece. The nozzle system is positioned with respect to the workpiece holder such that the fluid jet from the nozzle system contacts the workpiece. The apparatus also includes a media delivery system configured to output media. The media delivery system is positioned with respect to the nozzle system such that the fluid jet from the nozzles system carries the media outputted from the media delivery system against the workpiece.

In some embodiments, a method of processing a tubular workpiece includes delivering a fluid jet from a nozzle towards the workpiece. Media is delivered from a media delivery system towards at least one of the fluid jet or the workpiece. The tubular workpiece is moved with respect to the fluid jet. The media is carried against the workpiece with the fluid jet until forming a desired surface finish while moving the tubular workpiece.

In other embodiments, a luminal prosthesis for placement in a body lumen of a subject is prepared by a process including providing a tubular member having a first end, a second end, and a tubular main body extending between the first end and the second end. The tubular main body has an inner surface defining a central lumen and an outer surface for engaging the body lumen of the subject. A fluid jet is delivered along at least one of the inner surface and the outer surface of the luminal prosthesis to provide a desired surface finish to the at least one of the inner and outer surfaces.

In yet other embodiments, a tubular member has a first end, a second end, and a tubular main body extending between the first end and the second end. The tubular main body has an inner surface and an outer surface. The inner surface defines a central lumen having a diameter less than about 1 inch. The tubular member is prepared by delivering a fluid jet along at least one of the inner surface and the outer surface to provide a desired surface finish to the at least one of the inner and outer surfaces.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles may not be drawn to scale, and some of these elements may be arbitrarily enlarged and positioned to improve drawing legibility.

DETAILED DESCRIPTION OF THE INVENTION

The following description relates to processes and apparatuses for surface-finishing workpieces, such as tubular workpieces. The tubular workpieces can include, without limitation, deep narrow holes, through holes, highly curved surfaces, and the like. The apparatuses are disclosed in the context of surface-finishing through holes, unwanted surface topology, and curved surfaces because they have particular utility in this context. However, the apparatuses can be used in other contexts to perform other types of fabrication processes, such as cutting, milling, and the like, on other types of workpieces.

Unless the context requires otherwise, throughout the specification and claims which follow, the word "comprise" and variations thereof, such as, "comprises" and "comprising" are to be construed in an open, inclusive sense, that is as "including, but not limited to."

As used in this specification and the appended claims, the singular forms "a," "an," and "the" include plural referents unless the content clearly dictates otherwise. Thus, for example, reference to a workpiece including "a lumen"

includes a single lumen, or two or more lumens. It should also be noted that the term "or" is generally employed in its sense including "and/or" unless the content clearly dictates otherwise.

Figure 1:
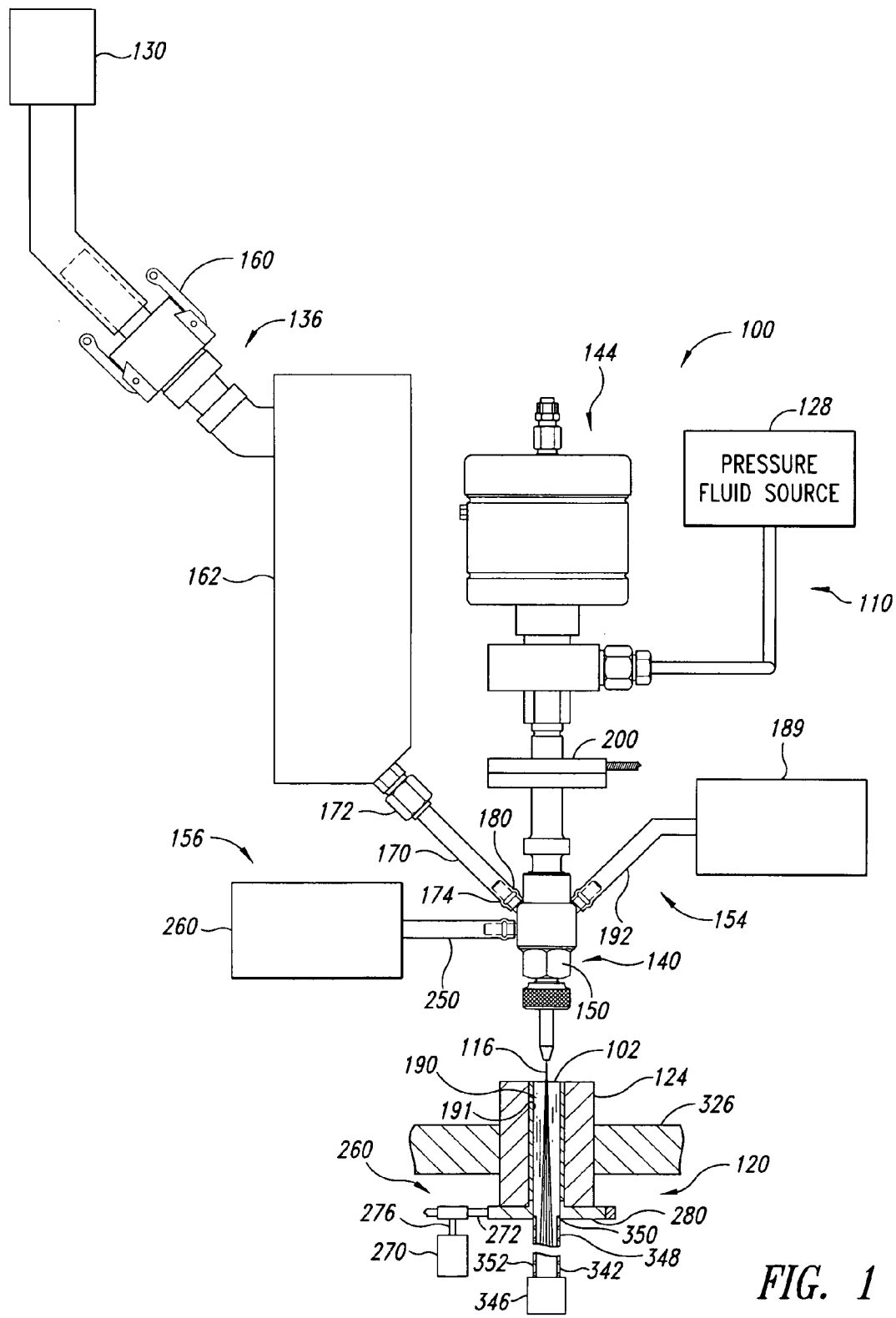
FIG. 1 is a partial cross-sectional, elevational view of a processing apparatus, in accordance with one illustrated embodiment.

FIG. 1 shows an apparatus 100 for processing a workpiece 102 (illustrated as a tubular member). Generally, the apparatus 100 includes a fluid jet delivery system 110 for outputting a fluid jet 116 and a holder system 120 for releasably retaining the workpiece 102. As used herein, and as discussed below, the term "fluid jet" may refer to a jet comprising only fluid or an abrasive fluid jet. The illustrated holder system 120 includes a rotatable holder 124 that can fixedly hold the workpiece 102 such that the fluid jet 116 can be moved relative to the workpiece 102 to produce a desired surface-finish.

The fluid jet delivery system 110 can include a pressure fluid source 128 configured to pressurize a fluid used to produce the fluid jet 116 and a media source 130 configured to provide media, such as abrasive particles. In the illustrated embodiment, media from the media source 130 flows through a media delivery system 136 and into a nozzle system 140. Pressurized fluid from the fluid source 128 flows through a fluid deliver system 144 and into the nozzle system 140. The nozzle system 140 combines the media and fluid to produce the fluid jet 116.

The media delivery system 136, pressurized fluid delivery system 144, and nozzle system 140 can cooperate to achieve a wide range of flow parameters of the fluid jet 116, including, without limitation, volumetric flow rate, flow velocity, level of homogeneity of the fluid jet 116, composition of the fluid jet 116 (e.g., ratio of media to pressurized fluid), and combinations thereof.

The nozzle system 140 has a mixing device 150 for controllably combining the pressurized fluid and media to produce the fluid jet 116 in the form of a surface-finishing fluid jet capable of producing various types of surface-finishes. In some embodiments, including the illustrated embodiment, the mixing device 150 is in fluid communication with a secondary pressurization system 154 for adjusting one or more flow parameters and a flushing system 156 configured to remove (periodically or continuously) at least a portion of the contents of the mixing device 150.

The fluid jet 116 can surface-finish or otherwise process the workpiece 102. The illustrated fluid jet 116, for example, in the form of a surface-finishing fluid jet can remove unwanted structural features (e.g., hanging burrs, protuberances, surface irregularities, rough or sharp edges, and the like), debris, contaminates, and other undesirable features often associated with conventional fabrication processes as noted above. The surface-finishing jet 116 can be a fan jet, round jet, or other type of high-pressure jet.

The term "burr" as used herein generally refers, without limitation, to deformed material (e.g., a metal) that forms a protuberance or raised or rough edge. The material can be deformed during a machining process (e.g., cutting, turning, milling, drilling, grinding, etc.), a laser cutting process, and the like. Burrs may be integrally connected to the workpiece and, thus, may be difficult to remove. In some embodiments, the fluid jet 116 can be used to roughen, smooth, cut, abrade, hone, polish, clean, or otherwise alter the surface texture or characteristics of the workpiece 102.

Various types of workpieces can be processed with the apparatus 100. Exemplary non-limiting workpieces include, without limitation, luminal prostheses (e.g., stents, stent grafts, and other intraluminal deployable devices), tubular members, or conduits, as well as other types of structures having relatively long and narrow lumens or deep holes. The subsystems, components, and features of the apparatus 100 discussed below can be modified or altered based on the configuration of the workpiece to be processed.

Referring again to FIG. 1, the media source 130 can contain media in the form of an abrasive that is ultimately entrained in the fluid jet 116. Although many different types of abrasives may be used, some embodiments use particles on the order of about 220 mesh or finer. The particular size can be selected based on the rate of abrasion and the desired surface textures (e.g., surface smoothness). The abrasive can be dry or wet (e.g., a wet abrasive in a slurry form) depending on whether the fluid jet 116 abrades, textures, cuts, etch, polishes, cleans, or performs another procedure.

The media source 130 can also have other types of media. For example, the media in the source 130 can be a fluid (e.g., liquid, gas, or mixture thereof used to clean, polish, cut, etch, and the like. For example, the media can be an etching fluid or acid (e.g., hydrochloric acid, nitric acid, hydrofluoric acid, sulfuric acid, fluorosulfuric acid, and other fluids capable of removing material from the workpiece) for enhancing the surface-finish of the workpiece 102. If etching fluids or acids are delivered through the apparatus 100, surfaces of the apparatus 100 in contact with these fluids can be treated or coated to reduce or limit damage to the apparatus 100. To clean the workpiece 102, the media can be in the form of a cleaner, including, without limitation, solvents (e.g., organic and/or inorganic solvents), degreasers, detergents, surfactants, and the like. Mineral spirits, acetone, and toluene are exemplary non-limiting solvents that can be readily delivered with the apparatus 100.

In some embodiments, the media source 130 can include a plurality of media types to perform different surface-finishing processes. For example, the media source 130 can output an abrasive to generate an abrasive fluid jet for rapidly removing unwanted features from the workpiece 102, and after the abrasion process, the media source 130 can output a cleaner to produce a cleaning fluid jet for removing unwanted contaminates or debris from the workpiece 102. The number, types, and properties of the media can be selected on a desired final surface-finish.

The illustrated media delivery system 136 extends from the media source 130 to the nozzle system 140 and, in one embodiment, includes an intermediate conduit 160 extending between the media source 130 and an optional air isolator 162. A media feed line 170 has an upstream end 172 and a downstream end 174 coupled to the air isolator 162 and a media inlet 180 (see FIG. 2), respectively. Media from the media source 130 can pass through the;, intermediate conduit 160, air isolator 162, and feed line 170 and into the media inlet 180.

The media flow rate into the nozzle system 140 can be increased or decreased based on the surface-finishing process to be performed. In some embodiments, the media is abrasive and the abrasive flow rate is equal to or less than about 7 lb/min (3.2 kg/min), 5 lb/min (2.3 kg/min), 1 lb/min (0.5 kg/min), or ranges encompassing such flow rates. In some embodiments, the abrasive flow rate is less than about 0.5 lb/min (0.23 kg/min) to produce an abrasive fluid jet 116 suitable for rapidly removing significant amounts of material from the interior regions of the illustrated workpiece 102 in the form of a stent. In some embodiments, the abrasive flow rate equal to or less than about 0.1 lb/min (0.05 kg/min) to produce an abrasive fluid jet 116 especially well suited for accurately removing unwanted targeted material with minimal impact to other untargeted material in proximity to the targeted material. With such a flow rate, the fluid jet 116 may be conveniently navigated through a lumen 190 of the workpiece 102 to remove material from the interior regions of the workpiece 102. For other types of media, the media flow rate can vary based on the surface-finishing process. For example, media in the form of a fluid may be delivered at high volumetric flow rate.

Additional types of media delivery systems can also be used. For example, a fluidized bed delivery system can controllably meter media to the nozzle system 140. The type of media delivery system can be selected based on desired metering capabilities.

With continued reference to FIG. 1, the secondary pressurization system 154 includes a secondary pressurization source 189 coupled to the nozzle system 140 via a pressurization line 192. In some embodiments, the pressurization source 189 includes a pump (e.g., a low pressure or vacuum pump) capable of applying a relatively low pressure or vacuum to adjust the pressure in the nozzle system 140. In some embodiments, the pressurization source 189 is capable of withdrawing at least some of the contents of the nozzle system 140 through the pressurization line 192 away from the nozzle system 140, thereby adjusting the performance of the apparatus 100.

The nozzle system 140 can be moved relative to the holder system 120. In some embodiments, including the illustrated embodiment of FIG. 1, an actuation system 200 is provided for selectively moving the nozzle assembly 140 with respect to the holder system 120. The actuation system 200 can be in the form of an X-Y positioning table driven by a pair of drive mechanisms. Motors (e.g., stepper motors) can drive the table to control the movement of the nozzle system 140. Other types of positioning systems employing linear slides, rail systems, motors, and the like can be used to selectively move and actuate the nozzle system 140 as needed or desired. U.S. Pat. No. 6,000,308, which is herein incorporated by reference in its entirety, discloses systems, components, and mechanisms that can be used to control the nozzle system 140.

Additionally or alternatively, the actuation system 200 can adjust the standoff distance so as to adjust the position of the fluid jet 116 axially with respect to the workpiece 102. Based on the size and configuration of the lumen 190, the standoff distance can be selected such that a substantial portion of the fluid jet 116 is sprayed into the lumen 190.

Figure 2:
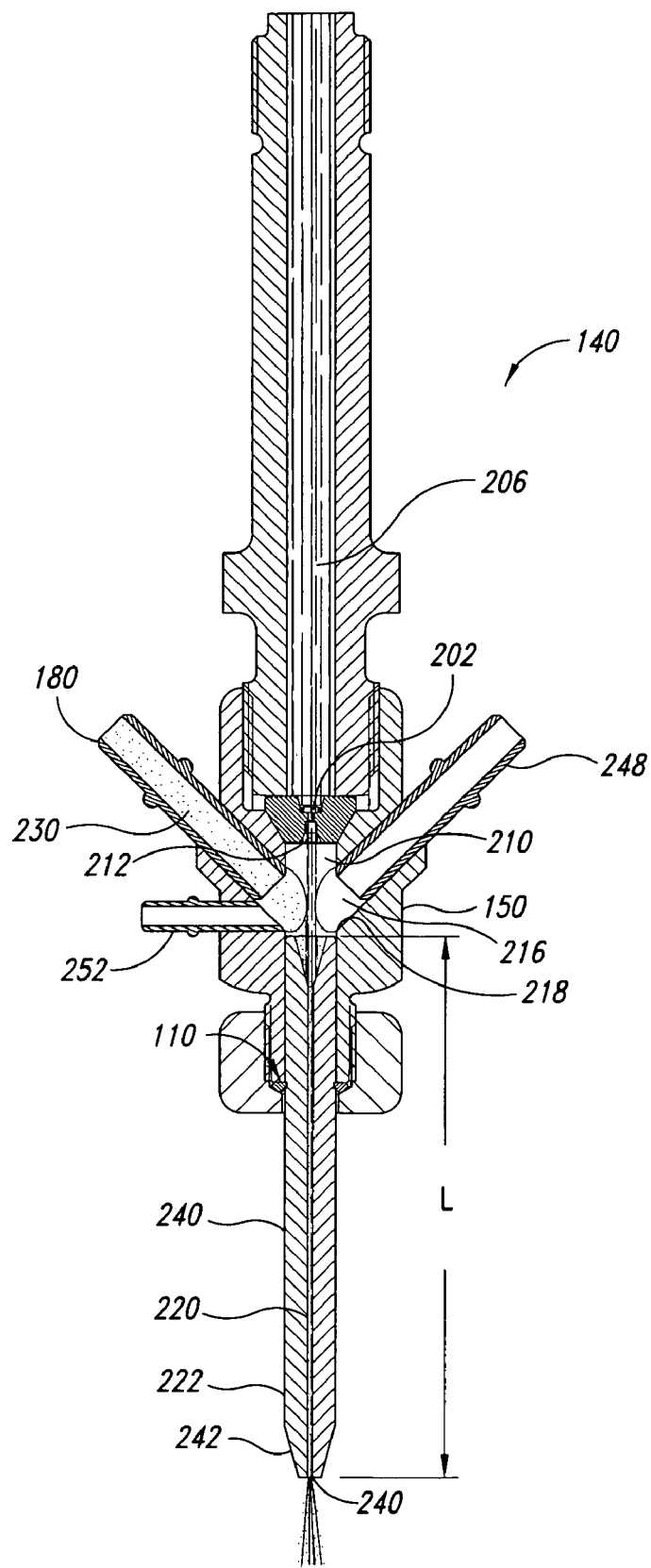
FIG. 2 is a cross-sectional view of a nozzle system for a processing apparatus, in accordance with one embodiment.

Referring to FIG. 2, the nozzle system 140 has an orifice 202 (illustrated within the mixing device 150), through which fluid 206 from the pressure fluid source 128 can pass to produce a fluid jet or cutting stream 210. Various types of orifices, jewels, or other fluid jet or cutting stream producing devices can be used to achieve the desired flow characteristics of the fluid jet 210. In some embodiments, the opening of the orifice 202 has a diameter in the range of about 0.001 inch (0.025 mm) to about 0.01 inch (0.25 mm). Openings with other diameters can also be used, if needed or desired.

The nozzle system 140 can be for ultrahigh pressures, medium pressures, low pressures, or combinations thereof. Ultrahigh pressure nozzle systems can operate at pressures equal to or greater than about 80,000 psi (551 MPa). High pressure nozzles can operate at a pressure in the range of about 60,000 psi (413 MPa) to about 80,000 psi (551 MPa). Medium pressure nozzles can operate at a pressure in the range of about 15,000 psi (103 MPa) to about 60,000 psi (413 MPa). Medium pressure nozzles operating at a pressure of about 40,000 psi (276 MPa) are especially well suited to process lumen walls of narrow tubes, such as stents. Low pressure nozzles can operate at a pressure in the range of about 10,000 psi (69 MPa) to about 40,000 psi (276 MPa). Low pressure nozzles operating at a pressure of about 15,000 psi (103 MPa) are especially well suited to process outside surfaces of narrow tubes (see FIG. 15).

The fluid jet 210 exiting the orifice 202 flows through a pressure fluid inlet 212 into and through a mixing chamber 216 defined by an interior surface 218 of the mixing body 150. The illustrated fluid jet 210 is generally axially aligned with a passageway 220 in a delivery conduit 222. To enhance the ability of the fluid jet 116 to remove material from a workpiece, the media delivery system 136 is coupled to the media inlet 180 through which media 230 (illustrated as abrasive particles) flows into the mixing chamber 216. The media 230 is then combined with the fluid jet 210 in the mixing chamber 216 to form a fluid jet 116 that proceeds into and through the passageway 220. The mixture proceeds along the passageway 220 and is ultimately emitted from an outlet 240 as the fluid jet 116.

The delivery conduit 222 can be a mixing tube, focusing tube, or other delivery tube or device configured to produce a desired flow (e.g., a coherent flow in the form of a round jet, fan jet, etc.). The illustrated delivery conduit 222 has a main body 240 extending away from mixing device 150 and terminating at a tip 242, which defines the outlet 240. In one embodiment, the tip 242 is configured to produce a round fluid jet.

The delivery conduit 222 can have a length L that is less than about 10 inches (25.4 cm). In some embodiments, the length L is in the range of about 0.2 inch (0.5 cm) to about 10 inches (25.4 cm). The diameter of the passageway 220 can be equal to or less than about 0.012 inch (0.35 mm). In some embodiments, the diameter of the passageway 220 is in the range of about 0.012 inch (0.35 mm) to about 0.05 inch (1.3 mm). The length L, diameter of the passageway 220, and other design parameters can be selected to achieve the desired mixing action as the fluid mixture passes through the delivery conduit 222.

The illustrated nozzle system 140 of FIG. 2 also includes a pressurization system connector 248 for coupling to the secondary pressurization system 154. As noted above, the pressurization system 154, in some embodiments, applies a low pressure, or a vacuum, to draw at least some of the contents (e.g., media, pressurized fluid, or both) of the mixing chamber 216 through the connector 248 and out of the nozzle system 140 in order to adjust the ratio of media to pressurized fluid in the fluid jet 116, distribution of the media in the fluid jet 116, volumetric flow rate of the fluid jet 116, and other flow criteria that effect the performance of the apparatus 100. In some embodiments, the pressurization system 154 helps draw the media 230 into the mixing chamber 216 towards the jet 210 to further control the amount of abrasive entrained in the fluid jet 116.

Referring again to FIGS. 1 and 2, the flushing system 156 is in fluid communication with mixing chamber 216 and can include a flushing line 250 coupled to a flushing inlet 252 of the nozzle system 140. A flushing fluid can flow through the flushing inlet 252 from the flushing line 250 and into the mixing chamber 216. The flushing inlet 252 can optionally include a valve (e.g., a check valve, globe valve, ball valve, and the like) for controlling flow through the inlet 252 into the mixing chamber 216. In some embodiments, for example, a check valve can allow flow through the inlet 252 into the nozzle system 140 and can block flow towards a flushing source 260.

The flushing source 260 can be a tank or reservoir for holding a flowable substance suitable for flushing. In other embodiments, the flushing source 260 is a fluid line connected to a fluid source, such as a water tap or spigot. The type of flushing source 260 can be selected based on the flushing operations to be performed.

To empty the mixing chamber 216, the flushing system 156 can selectively inject a desired amount of fluid from the flushing source 260 through the flushing line 250 and the inlet 252 and into the nozzle system 140. The flushing source 260 can include a pump (e.g., a low pressure pump or vacuum pump) that operates to flush the nozzle system 140. In other embodiments, the pressurized fluid from the pressure fluid source 128 can be used to carry out unwanted media in the mixing chamber 216 after flushing fluid enters via the inlet 252. The pressurized fluid can flow into the mixing chamber 216. The fluid then circulates through the mixing chamber 216 and carries media from the mixing chamber 216 through the outlet 240, with or without any applied low pressure or vacuum from the secondary pressurization source 189.

The mixing chamber 216 can be periodically flushed to limit or substantially eliminate buildup (e.g., media buildup) therein. The flushing process can also be preformed before introducing different medias through the nozzle system 140, thereby limiting or preventing contamination between different processing sequences. In some embodiments, the mixing chamber 216 is flushed in-between the processing of workpieces. After processing the illustrated workpiece 102, for example, at least a portion of the contents of the mixing chamber 216 can be discharged to the pressure fluid source 128 and/or out of the nozzle system 240. During this flushing process, the flow of media 230 through the media inlet 180 can be reduced or stopped in order to empty the mixing chamber 216. After the flushing process, another workpiece can be processed with the same or in different media. Additionally or alternatively, the flushing process can be performed when the workpiece 102 is reoriented (e.g., reversed), as detailed further below.

Figure 3:
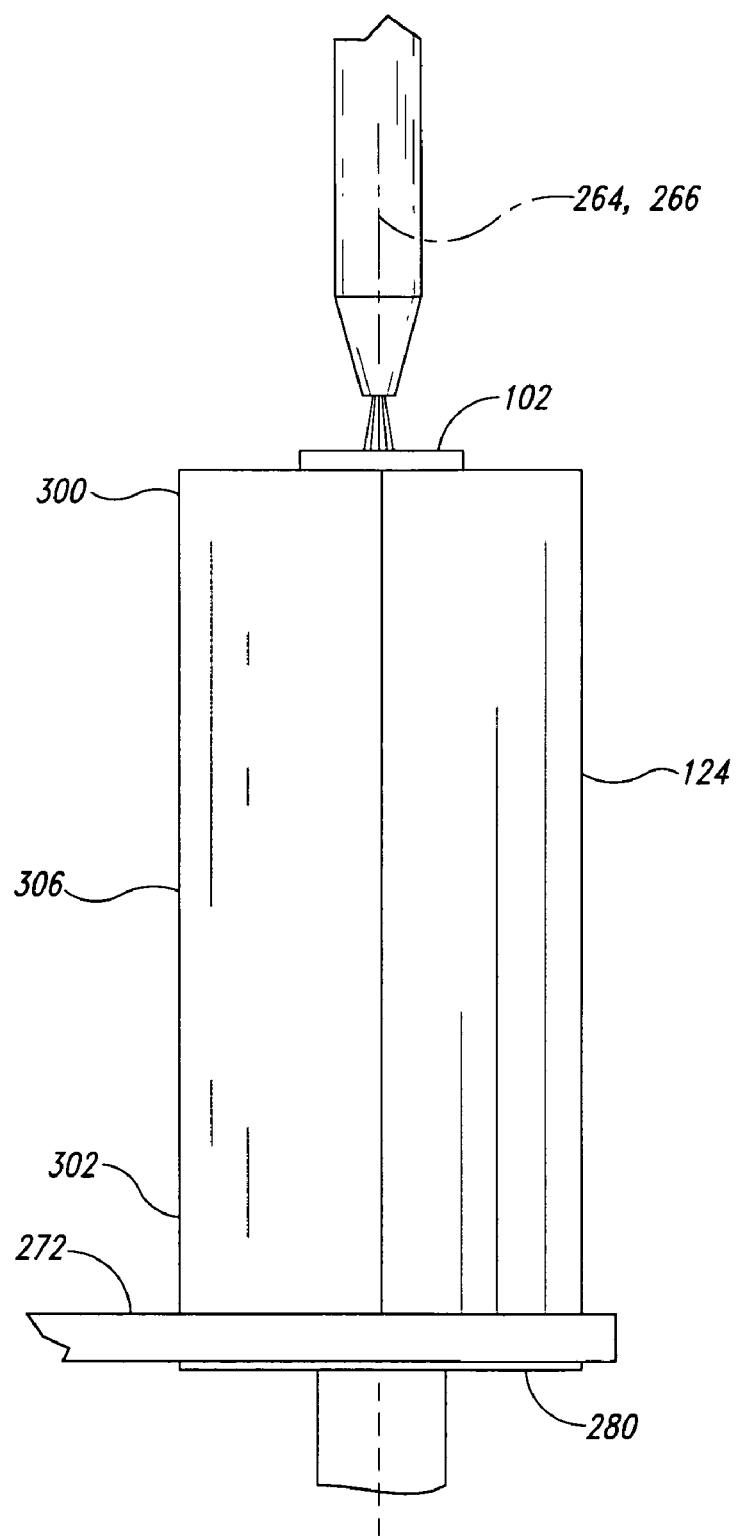
FIG. 3 is a side elevational view of several elements of the processing apparatus of FIG. 1.
Figures 4A, 4B:
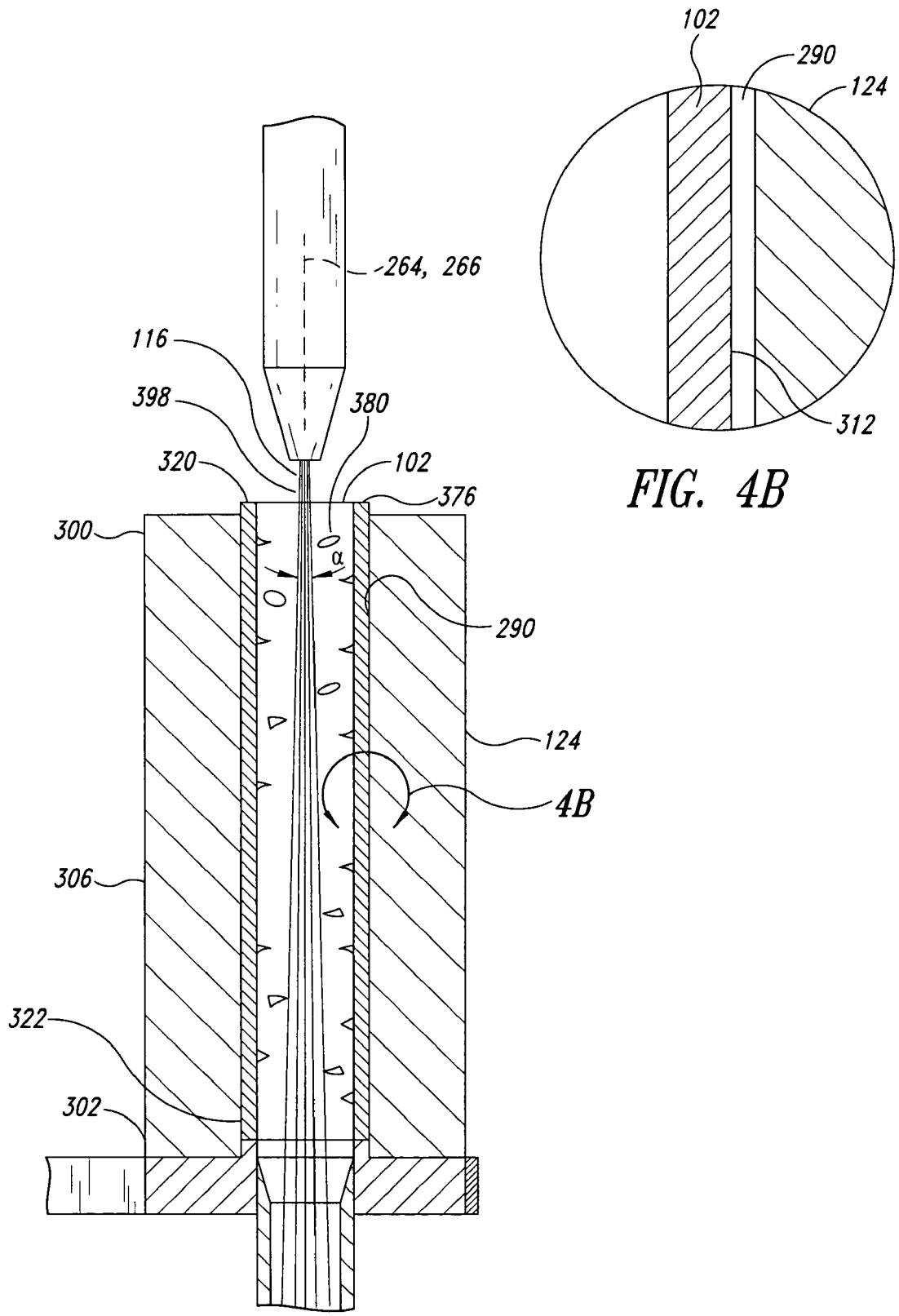
FIG. 4A is a partial cross-sectional, elevational view of the elements of FIG. 3.
FIG. 4B is an enlarged cross-sectional view of a portion of the elements of FIG. 4A.

With continued reference to FIG. 1, the holder system 120 includes a drive system 260 coupled to the rotatable holder 124. The illustrated drive system 260 rotates the holder 124 and workpiece 102 together about an axis of rotation 264 (see FIGS. 3 and 4A) as the fluid jet 116 flows through the workpiece 102, thereby producing a somewhat uniform finish along the inner periphery of the workpiece 102. As shown in FIGS. 3 and 4A, a longitudinal axis 266 of the workpiece 102 can be proximate (e.g., aligned, collinear, and the like) the axis of rotation 264. The illustrated workpiece 102 and holder 124 are generally concentric.

The drive system 260 can include a drive motor 270 coupled to the rotatable holder 124 via a flexible drive member 272 (e.g., a drive chain, drive belt, and the like). The flexible drive member 272 can form a loop surrounding both a drive shaft assembly 276 driven by the motor 270 and a retainer 280 coupled to the rotatable holder 124. When energized, the drive motor 270 thus drives the holder 124 through the flexible drive member 272 at a desired rotational speed. In some embodiments, the drive motor 270 can rotate the workpiece 102 at a rotational speed greater than about 500 RPM. In some embodiments, the workpiece 102 is rotated at a rotational speed in the range of about 500 RPM to about 1,500 RPM. During a deburring process, for example, the workpiece 102 can be rotated at a rotational speed of about 1000 RPM. Other drive systems and drive arrangements can selectively rotate the holder 124.

With reference now to FIGS. 3, 4A and 4B, the holder 124 defines a receiving chamber 290 in which the workpiece 102 can be placed. The illustrated holder 124 has an upper portion 300, a lower portion 302 for coupling to the retainer 280, and a central body 306 extending therebetween. An inner surface 310 of the holder 124 defines the chamber 290 and is dimensioned for closely receiving the workpiece 102. During processing, the inner surface 310 can be pressed against an outer surface 312 of the workpiece 102 to reduce, limit, or substantially prevent movement of the workpiece 102 relative to the holder 124. Accordingly, clamping forces can be selected and applied to achieve the desired interference fit between the workpiece 102 and the inner surface 310 of the holder 124. Additionally or alternatively, various types of keying features (e.g., protrusions, recesses, bosses, and the like) can be used to limit or substantially prevent relative movement between the workpiece 102 and the holder 124.

The configuration of the chamber 290 can be generally similar to the configuration of the workpiece 102, resulting in a close fit. The axial cross-sectional profile of the chamber 290, for example, can be generally similar to the axial cross-sectional profile of the workpiece 102. The illustrated chamber 290 of FIGS. 4A and 4B is in the form of a through hole extending between the upper and lower portions 300, 302. In one embodiment, a first end 320 of the illustrated cylindrical workpiece 102 is proximate the upper portion 300 and an opposing second end 322 of the workpiece 102 is proximate the lower portion 302.

Figure 5:
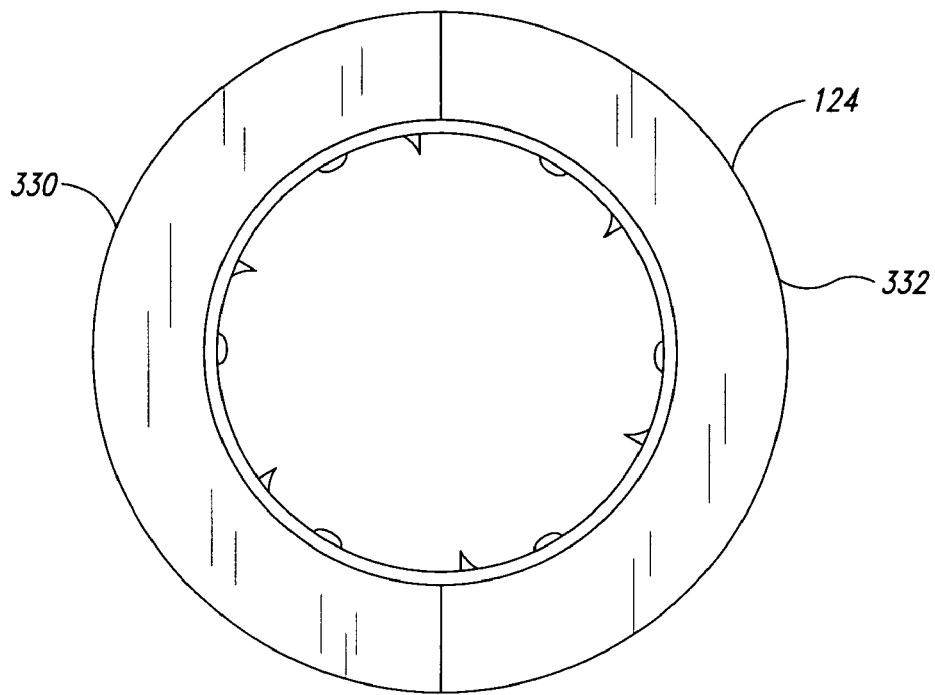
FIG. 5 is a plan view of a workpiece in a holder, wherein the holder is in a closed position.
Figure 6:
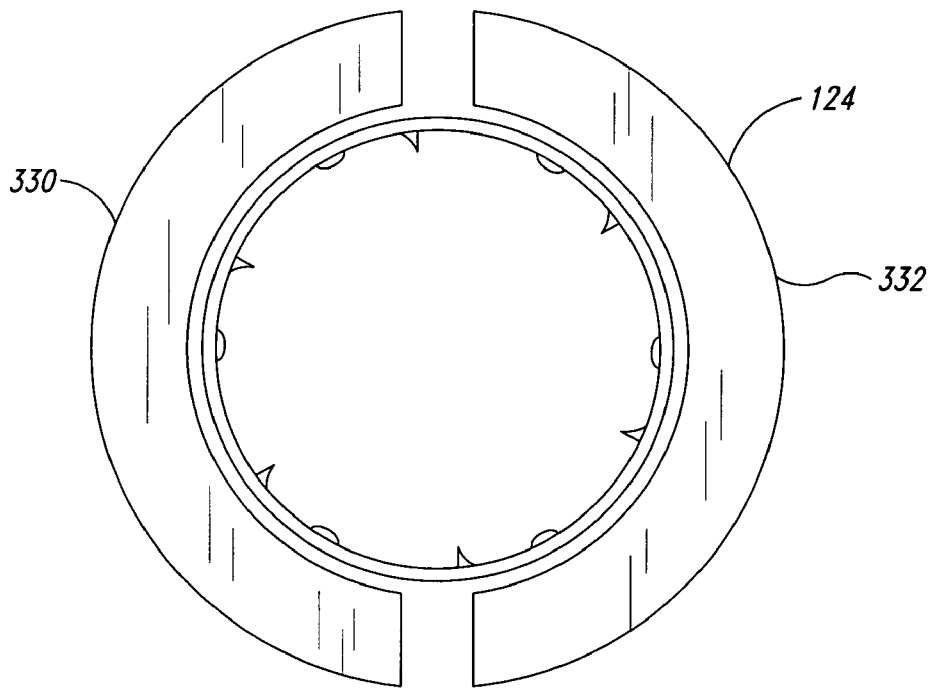
FIG. 6 is a plan view of the workpiece and holder of FIG. 5, wherein the holder is in an open position.

FIGS. 5 and 6 show the holder 124 in a closed position and an open position, respectively. The holder 124 can include a pair of mating halves 330, 332 moveable between the closed position for securely holding the workpiece 102 and the open position for removing, replacing, or repositioning the workpiece 102. For example, the holder 124 in the closed position of FIG. 5 can fixedly retain the workpiece 102 during the surface-finishing process. Once the surface-finishing process is completed, the holder 124 can be moved outwardly towards the open position of FIG. 6 to release the workpiece 102.

Figure 10:
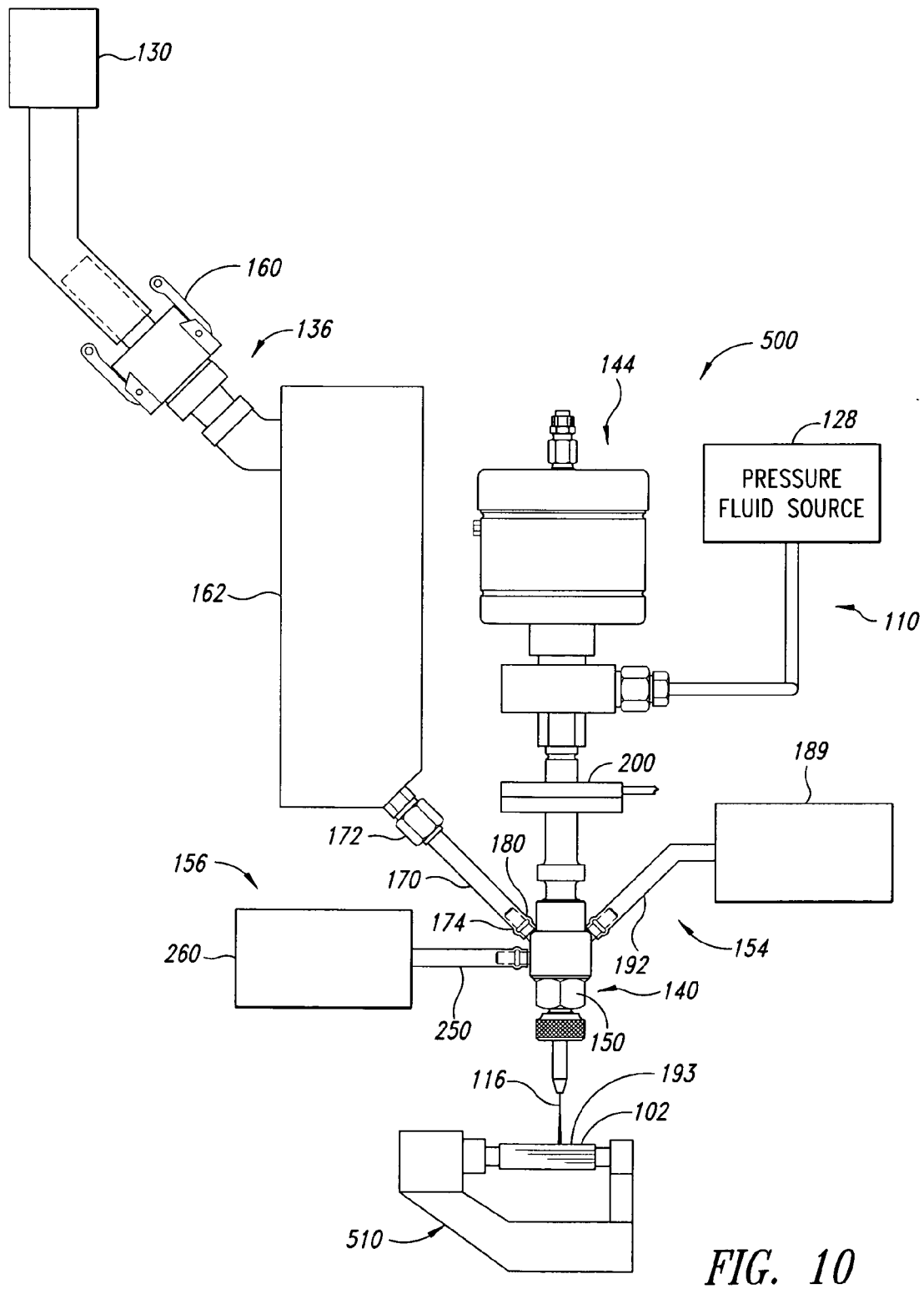
FIG. 10 is a side elevational view of a processing apparatus, in accordance with one illustrated embodiment.
Figure 17:
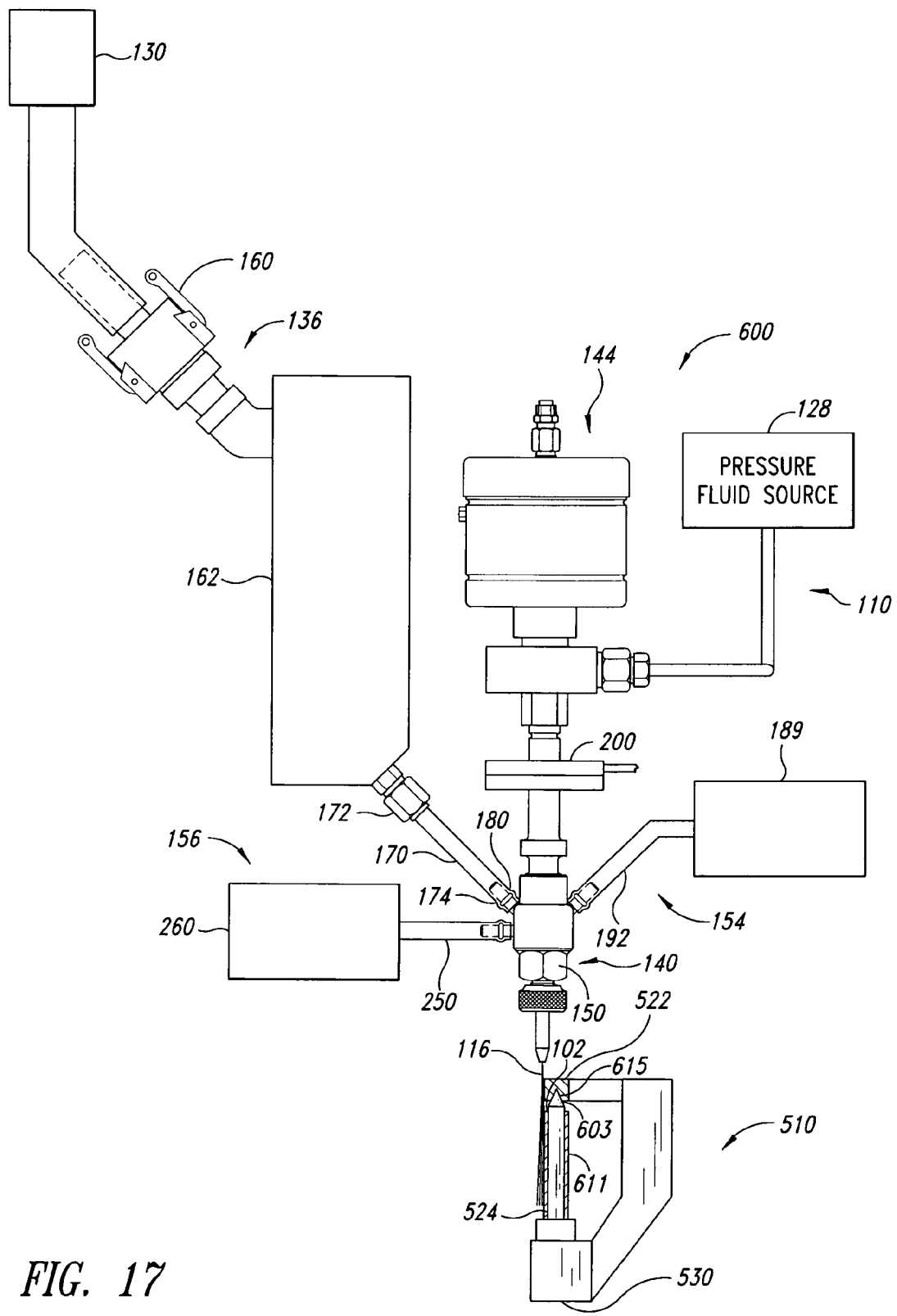
FIG. 17 is a side elevational view of a processing apparatus, in accordance with one illustrated embodiment.

The holder system 120 can include other types of holders for retaining the work piece 102. Exemplary holders include, but are not limited to, one-piece tubular holders, multi-piece tubular holders, sleeves (including split sleeves), combinations thereof, and other fixture devices for releasably retaining the workpiece 102. The configuration of the holder can be chosen based on the configuration of the workpiece to be processed. For example, FIGS. 10 and 17 illustrate holders suitable for holding a workpiece 102 during exterior surface processing.

With reference again to FIG. 1, the holder system 120 can include a support member 326 rotatably retaining the holder 124. Journal bearings, sleeve, bearings, and other types of bearings can be used to permit rotation of the axially fixed holder 124. If large amounts of material are rapidly removed from the workpiece 102, bearings (e.g., roller thrust bearings) designed to withstand large axial loads (e.g., thrust loads) can be employed.

A discharge system 342 for removing used processing material (e.g., pressurized fluid, media, or both) can be in fluid communication with the holder system 120. After the fluid jet 116 processes the workpiece 102, it flows out of the holder system 120 via the discharge system 342. In this manner, the system 342 can controllably evacuate the holder system 120.

The discharge system 342 can include a pressurization device 346 and an output line 348 extending between the holder system 120 and the pressurization device 346. An upstream end 350 of the output line 348 can be temporarily or permanently coupled to the holder system 120 and a downstream end 352 of the output line 348 can be temporarily or permanently coupled to the pressurization device 346. The output line 348 can comprise one or more hoses, pipes, conduits, or other structures through which fluid can flow.

The pressurization device 346 can vacuum assist the surface-finishing process to adjust system performance and can also help remove and collect spent processing material. In some embodiments, the discharge system 342 does not apply any pressure (negative or positive). In some embodiments, the discharge system 342 is in the form of a catchtank or waste receptacle for receiving and storing spent fluid, abrasives, and the like.

To flush the apparatus 100, fluid from the flushing source 260 can flow through the mixing chamber 216 and workpiece 102 and into the discharge system 342 while the fluid jet 116 may be flowing. The flushing cycle can be performed until the desired amount of media is evacuated from the apparatus 100.

In some embodiments of surface-finishing, the apparatus 100 delivers the fluid jet 116 through the central lumen 190 of the workpiece 102, which is releasably coupled to the holder 124. The fluid jet 116 can be positioned generally concentrically or eccentrically with respect to the workpiece 102. For example, the jet 116 may be moved with respect to the inner surface 191 of the workpiece 102 such that it contacts the targeted material. During this processes, the holder system 120 can rotate the workpiece 102 to promote a somewhat uniform finish along the inner circumference of the workpiece.

The pressure fluid source 128 can supply a gas-phase fluid (e.g., air), a liquid-phase fluid (e.g., water, saline, and the like), or mixtures thereof. The fluid source 128 can also include pressurizing means, such as a pump with an intensifier or another high-pressure device, for pressurizing fluid up to and in excess of about 100,000 psi (689 MPa). For example, direct drive pumps capable of generating pressures up to about 55,000 psi (379 MPa) and pumps with intensifiers capable of generating pressures up to and in excess of about 100,000 psi (689 MPa) are available from Flow International Corporation of Kent, Wash. The pressure of the fluid from the fluid source 128 can be adjusted to correspondingly adjust the velocity of the fluid jet 116.

The fluid jet 116 can be positioned generally concentrically with respect to the axis of rotation 264 and/or the workpiece 102. A spread angle α (see FIG. 4A) can be adjusted to provide the desired coverage of the inner surface of the workpiece 102. For example, the spread angle α can be increased until the fluid jet 116 contacts the target material of the workpiece 102 to be removed. The fluid jet 116 can flow against and cut material (e.g., burrs) extending into the lumen 190. As used herein, the term "cut" generally refers, without limitation, to the separating of material from a workpiece. In some embodiments, the fluid jet 116 cuts the workpiece 102 by abrading or gradually wearing away material from the workpiece 102.

The spreading angle α (FIG. 4A) of the fluid jet 116 can be increased or decreased to move fluid jet 116 towards or away from a sidewall 376 of the workpiece 102 to achieve the desired surface textures (e.g., roughness, waviness, and form). For example, the fluid jet 116 can have a sufficiently high cutting capability to remove protuberances 380 (e.g., hanging burrs) it contacts so as to form a substantially burr free section of the lumen 190. These protuberances 380 may have been formed during a fabrication process, such as a machining process, cutting process (e.g., machine cutting, laser cutting, and the like), and other processes that may appreciably affect the topography of the workpiece 102. For example, the workpiece 102 may include a lattice structure formed by beams, structures, ribs, elongate members, and the like that are formed by a lattice machining processes (e.g., machining, drilling, cutting including laser cutting, etc.). Unwanted features, which may be formed by these processes, can be conveniently removed with minimal or substantially no collateral damage to the lattice structure.

Figure 7:
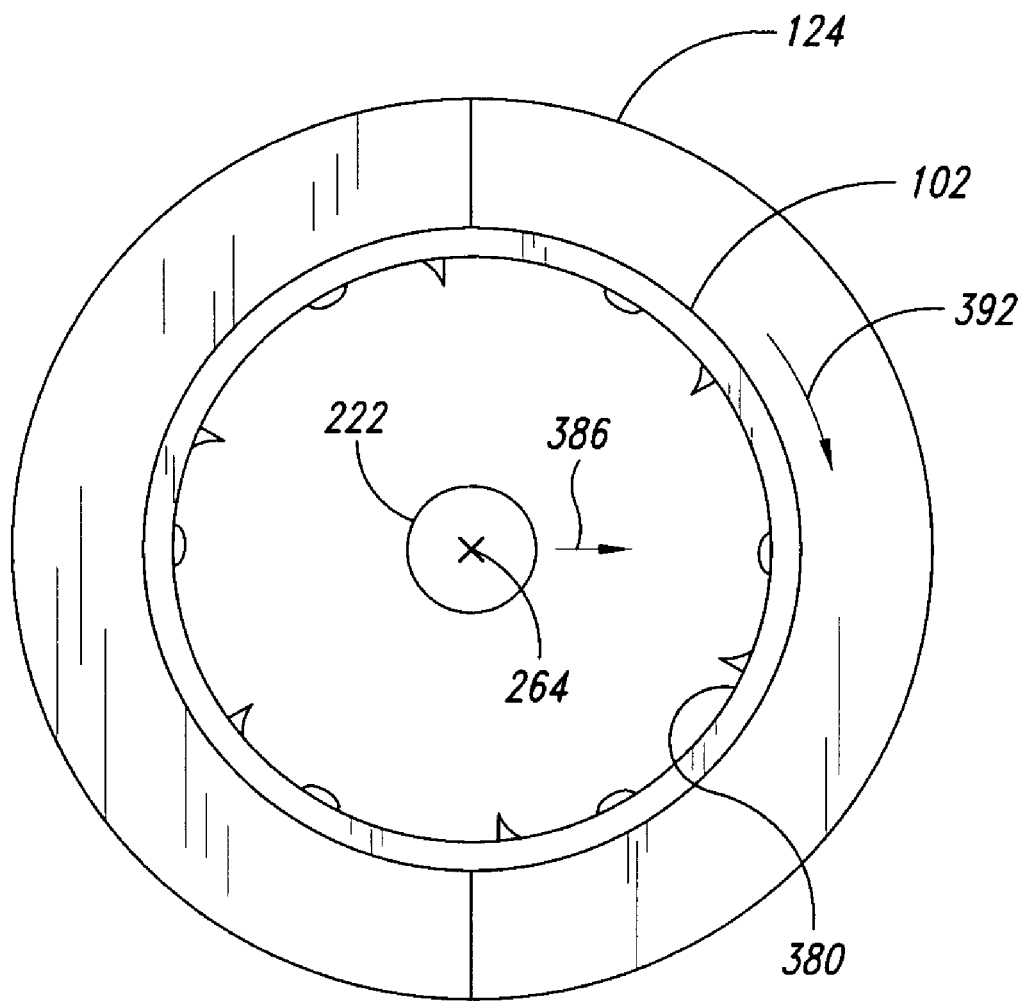
FIG. 7 shows a delivery conduit for emitting a fluid jet moving with respect to a workpiece in a holder.

In some embodiments, the fluid jet 116 is moved radially relative to the workpiece 102. As shown in FIG. 7, the delivery conduit 222 can be moved radially away from the axis of rotation 264 (indicated by the arrow 386) to gradually remove material from the inner periphery 191 of the workpiece 102. During this process, the workpiece 102 can be rotated, for example, in the clockwise direction (indicated by the arrow 392). Once the fluid jet 116 touches the protuberances 380, the fluid jet 116 can reduce the size of the protuberances 380, and if the jet 116 is moved further outward, it can remove the protuberances 380 altogether. Accordingly, the fluid jet 116 can form a substantially protuberance free inner surface 191 of the workpiece 102. In some embodiments, the fluid jet 116 is used to increase the nominal diameter of the lumen 190, or to otherwise alter the geometry of the workpiece 102.

Once the fluid jet 116 contacts the curved inner surface 191 (illustrated as a generally cylindrical surface), the fluid jet 116 can adjust surface texture parameters, such as average surface roughness (Ra), height of the highest peak (Rp), or depth of the deepest valley (Rv), for a target area. In some embodiments, the surface roughness Rz is reduced by at least about 10%, 40%, 50%, 80%, or ranges encompassing such percentages.

In some embodiments, after processing the workpiece 102, the position of workpiece can be reversed. For example, the illustrated workpiece 102 can be flipped such that the first end 320 is adjacent the retainer 280 and the second end 322 extends outwardly from the holder 124. In the embodiment of FIG. 4A, for example, the fluid jet 116 flows through the workpiece 102 until a desired amount of surface-finishing has been achieved. The workpiece 102 is then flipped such that the fluid jet 116 flows through the workpiece 102 in the opposite direction relative to the lumen 190. Thus, the jet 116 can flow in substantially opposite directions through the lumen 190. In this manner, both ends of the inner surface 191 can be separately processed for a substantially uniform finish along the axial length of the surface 190.

Figure 8:
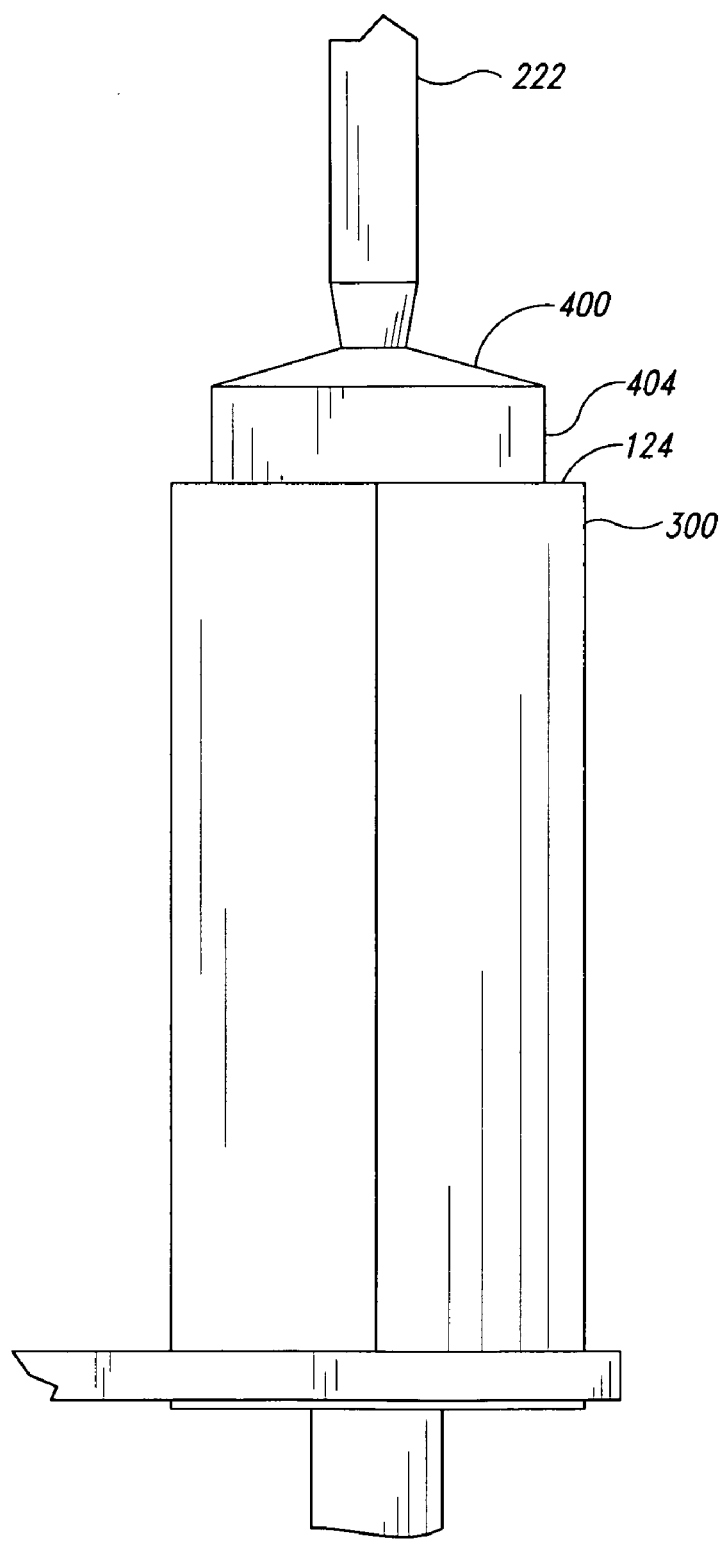
FIG. 8 is a side elevational view of a portion of a processing apparatus, in accordance with one illustrated embodiment.
Figure 9:
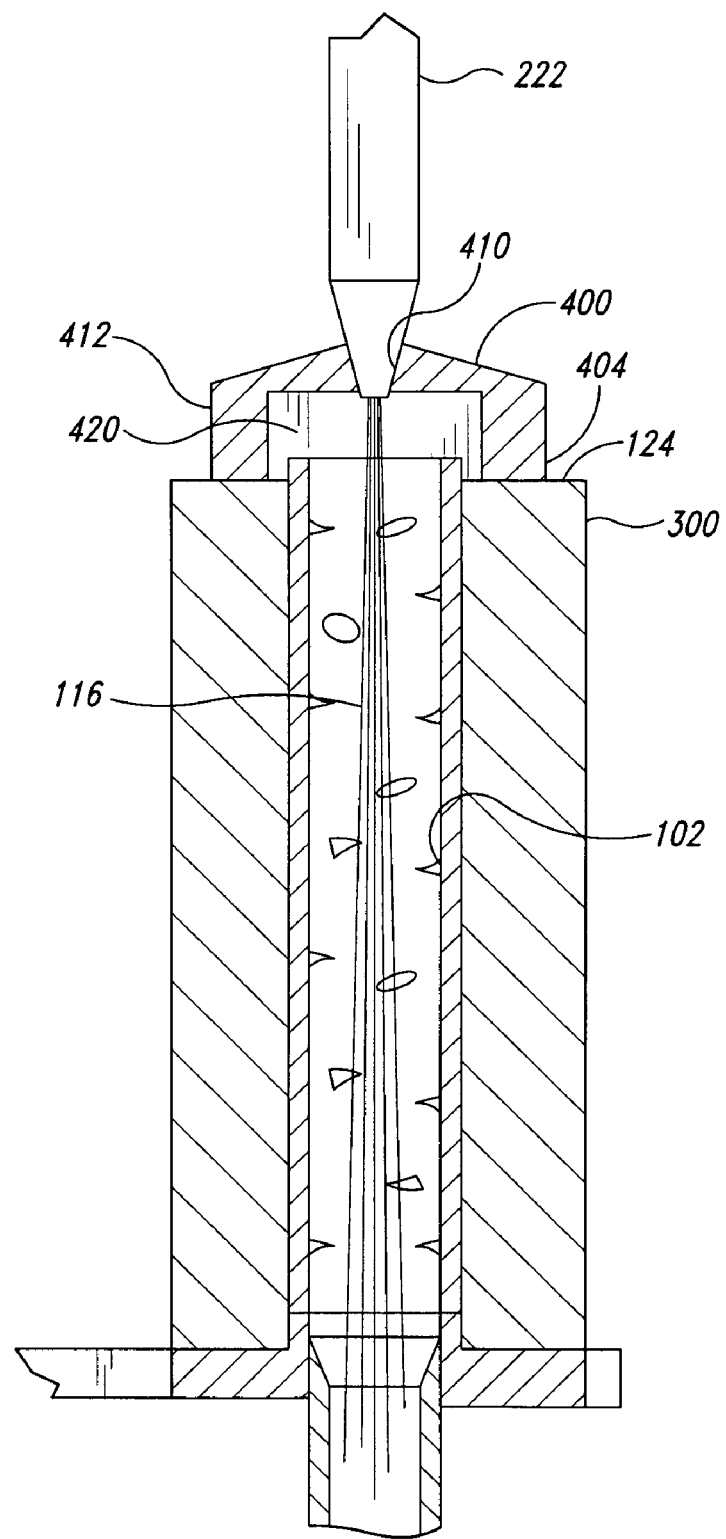
FIG. 9 is a partial cross-sectional view of the portion of the processing apparatus of FIG. 8.

FIGS. 8 and 9 illustrate a positioning device 400 that can be used to position the fluid jet 116 with respect to the workpiece 102. The illustrated positioning device 400 extends between the delivery conduit 222 and holder 124 and includes a mounting portion 404 for coupling to the upper portion 300 of the holder 124, an engagement portion 410 for engaging the delivery conduit 222, and a positioning main body 412 extending between the mounting portion 404 and engagement portion 410. When installed, a main passageway 420 extends from the delivery conduit 222 to the workpiece 102, thereby defining a fluid pathway for the fluid jet 116.

The positioning device 400 can be fixedly coupled to the holder 124 such that the positioning device 400 and holder 124 rotate together. During rotation, the engagement portion 410 slidably retains the delivery conduit 222 to reduce or limit any unwanted movement (e.g., axial movement, lateral movement, or both) of the fluid jet 116 for consistent and repeatable positioning. In some embodiments, including the illustrated embodiment of FIG. 9, the engagement portion 410 defines a somewhat frusto-conical bearing surface that surrounds the outer periphery of the delivery conduit 222 to maintain a generally concentric alignment of the fluid jet 116 and workpiece 102.

The illustrated positioning device 400 can be removed from the holder 124 to perform surface-finishing procedures requiring eccentric positioning of the jet 116 relative to the workpiece 102. In other embodiments, the positioning device 400 can be integrated into the holder 124 to reduce the number of separate components. The holder 124 and positioning device 400, for example, can be monolithically formed to further limit movement therebetween.

Exemplary positioning devices can include, without limitation, one or more bushings, bearings, and other types of members or devices providing a seating surface. To reduce friction during rotation of the workpiece 102, the positioning device 400 can include a bearing or low friction surface that engages the cylindrical outer surface or tapered surface of the delivery conduit 222.

FIG. 10 shows an apparatus for processing the outer periphery 193 of the workpiece 102. Generally, the apparatus 500 includes the fluid jet delivery system 110 and a holder system 510 for holding and positioning the workpiece 102 with respect to the fluid jet 116. The illustrated apparatus 500 can be used to perform various surface-finishing procedures on the rotating workpiece 102, and may be generally similar to the apparatus 100 illustrated in FIG. 1, except as further detailed below.

Figure 11:
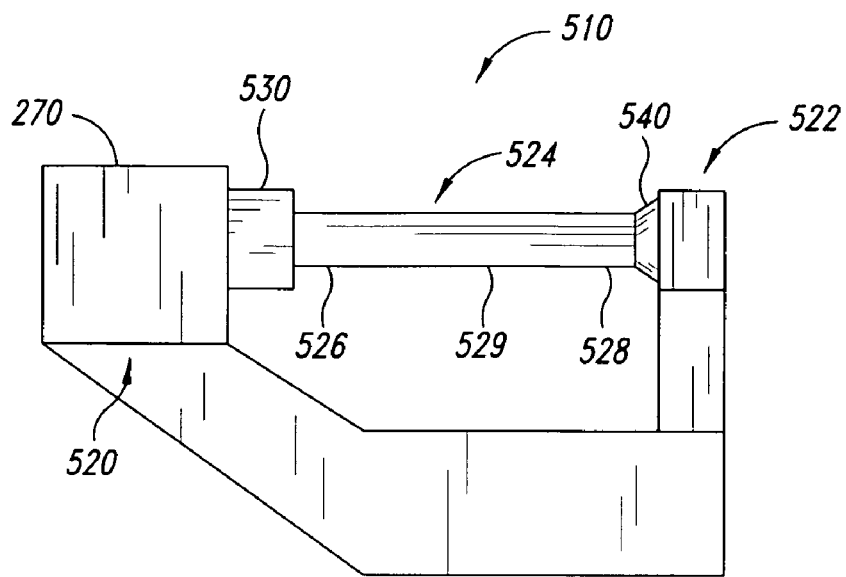
FIG. 11 is a side elevational view of several elements of the processing apparatus of FIG. 10.
Figure 12:
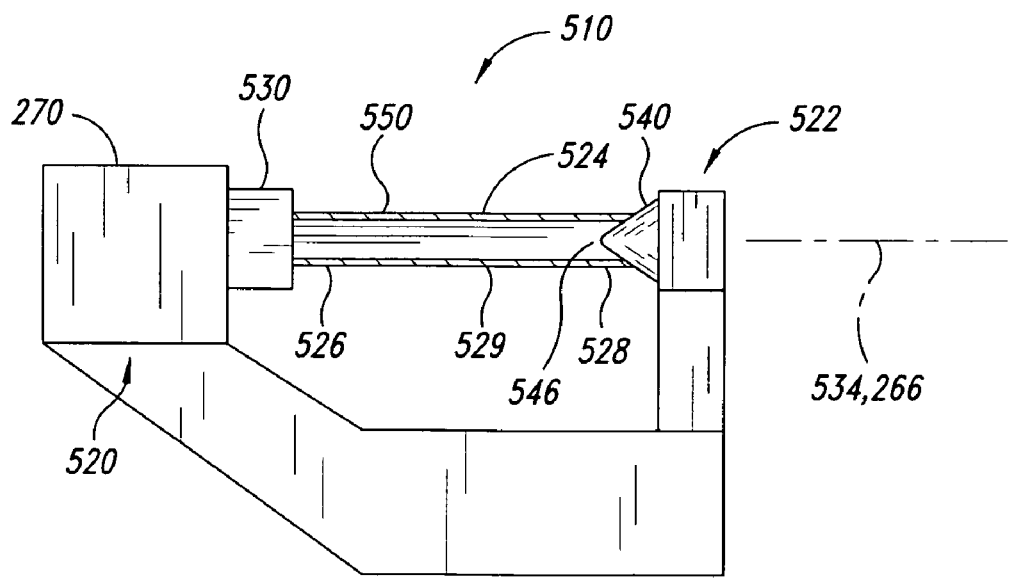
FIG. 12 is partial cross-sectional, elevational view of the several elements of the processing apparatus of FIG. 11.

FIGS. 11 and 12 show the holder system 510 (shown empty without the workpiece 102) including a drive system 520, mandrel holder 522, and mandrel 524 extending between the drive system 520 and the holder 522. The mandrel 524 includes a first end 526, a second end 528 opposing the first end 526, and a main body 529 extending between the first and second ends 526, 528. The first and second ends 526, 528 engage the drive system 520 and mandrel holder 522, respectively. To load the holder system 510, the mandrel 524 can be inserted through the lumen of the workpiece 102.

The drive system 520 includes a drive motor 270 and a rotatable retainer 530 detachably coupled to the mandrel 524. The mandrel 524 rotates about an axis of rotation 534 when the drive motor 270 is energized. When the workpiece 102 is placed on the mandrel 524 (shown in FIG. 10), the drive motor 270 controllably rotates the mandrel 524 and workpiece about the axis of rotation 534.

The retainer 530 can be a chuck (e.g., a lathe chuck), clamp, or other device suitable for clamping onto and centering the mandrel 524. For example, the retainer 530 can be a chuck having a plurality of movable jaws that cooperate to receive, center, and clamp onto the mandrel 524. Other connecting means can be used to connect the mandrel 524 and the motor 270.

The mandrel holder 522 of FIG. 12 includes a positioner 540 and a bearing system 544 that pivotally retains the positioner 540. The positioner 540 extends through a passageway 546 at the second end 528 of the mandrel 524. The distance between the bearing system 544 and retainer 530 can be selected to ensure that the positioner 540 remains in the passageway 546. The illustrated positioner 540 is somewhat conical in shape and, thus, can fit in passageways having various sizes and geometries. However, the positioner 540 can also have other shapes depending on the configuration of the mandrel 524. For example, the positioner 540 can be configured to engage a mandrel terminating in a conical tip.

The positioner 540 can help maintain proper alignment of the mandrel 524, even when appreciable side loads are applied to the workpiece 102. In the illustrated embodiment of FIGS. 11 and 12, the mandrel holder 522 and retainer 520 cooperate to maintain proper centering of the mandrel 524 about the axis of rotation 534 throughout the surface-finishing process.

The mandrel 524 is a tubular member dimensioned to fit inside the tubular workpiece 102. In some embodiments, the mandrel 524 is a split mandrel having movable sections for accommodating workpieces of different sizes. An actuatable member is moved through the spit mandrel to move the movable sections radially outward or inward. In other embodiments, the mandrel 524 is a solid rod having a recess or longitudinal passageway sized to receive the positioner 540. The configuration and dimensions of the mandrel 524 can be selected based on the configurations of the workpiece 102 and holder system 510. Exemplary mandrels can have generally circular axial profiles, polygonal (including rounded polygonal) axial profiles, elliptical axial profiles, and other axial profiles that may generally match the profiles of the tubular member disposed thereon.

The mandrel 524 can be formed, in whole or in part, of a high wear material for a prolonged working life. In such embodiments, the mandrel 524 can be formed, in whole or in part, of a hardened material that can be repeatedly exposed to the fluid jet. The hardened material can be harder than the material forming the workpiece 102, such that the workpiece 102 can be processed with the fluid jet 116 while keeping damage to the mandrel 524 at or below an acceptable level. The mandrel 524, for example, can erode less than the workpiece 102 when both the mandrel 524 and workpiece 102 are contacted by the fluid jet 116. After surface processing, the workpiece 102 can be easily removed from the mandrel 524 because of the mandrel 524 retaining its original shape.

Hardened materials may include, without limitation, tungsten carbide, titanium carbide, and other abrasion resistant or high wear materials that can withstand exposure to the fluid jets disclosed herein. Various types of testing methods (e.g., the Rockwell hardness test or Brinell hardness test) can be used to determine the hardness of a material. In some non-limiting exemplary embodiments, the mandrel 524 is made, in whole or in part, of a material having a hardness that is greater than about 3 $R_c$ (Rockwell, Scale C), 5 $R_c$, 10 $R_c$, or 20 $R_c$ than the hardness of the workpiece 102. In some embodiments, an outer surface 550 (or other portion(s) of the mandrel 524) is formed, in whole or in part, of a material having a hardness greater than about 62 $R_c$, 64 $R_c$, 66 $R_c$, 67 $R_c$, and 69 $R_c$, or ranges encompassing such hardness values.

Figure 13:
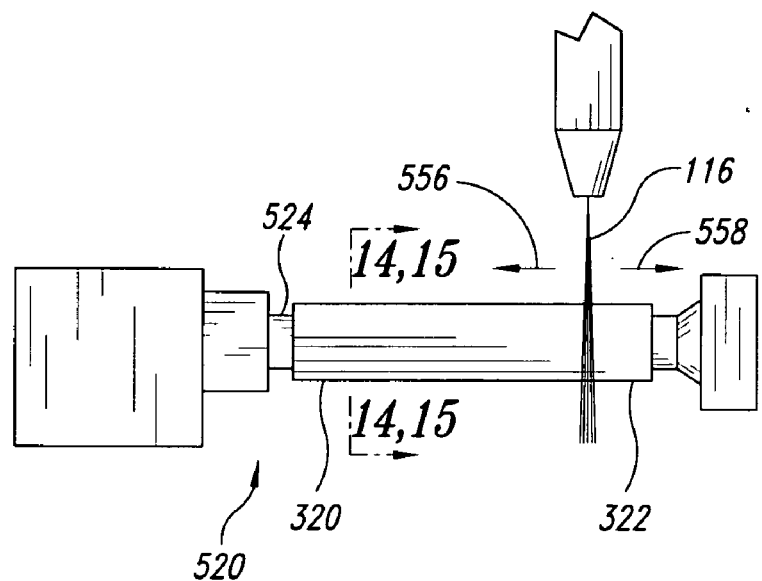
FIG. 13 is a side elevational view of a workpiece being processed by a water jet, in accordance with one illustrated embodiment.
Figure 14:
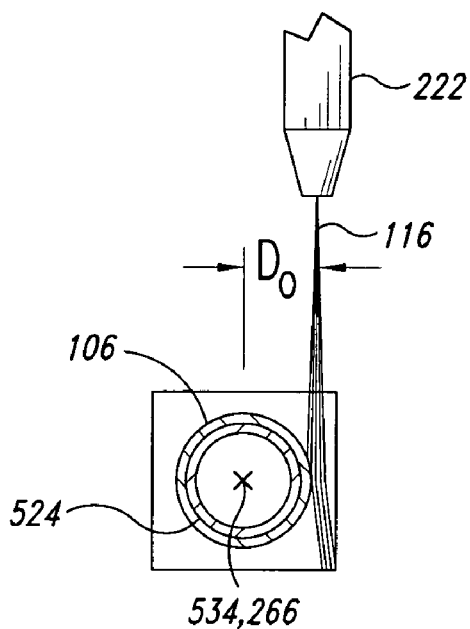
FIG. 14 is a cross-sectional view of the workpiece and mandrel disposed therethrough taken along a line 14-14 of FIG. 13.

FIGS. 13 and 14 show the fluid jet 116 contacting the workpiece 102 positioned on the mandrel 524. The fluid jet 116 is a round fluid jet for providing highly localized surface-finishing. The fluid jet 116 flows along a flow path that is spaced, or radially offset, a distance $D_o$ from the axis of rotation 534, thereby contacting an outermost section of the surface of the workpiece 102. The distance $D_o$ can be increased or decreased to adjust the size of the area being processed. For a deburring process, the distance $D_o$ can be chosen such that the portion of the fluid jet 116 flowing against the burrs has a sufficient cutting or abrading capacity for rapidly removing the burrs. For texturing the workpiece 102, the distance $D_o$ can be reduced to increase the area contacted by the fluid jet 116.

During surfacing finishing, the workpiece 102 can be rotated at a constant, varying rotational speed, or both. The fluid jet 116 can be moved linearly and longitudinally along the length of the rotating workpiece 102, as indicated by the arrows 556, 558 of FIG. 13. In one embodiment of processing, the fluid 116 first strikes the first end 320 of the workpiece 102 and then sweeps along the length of the workpiece 102 to the second end 322 of the workpiece 102. The drive system 520 continuously rotates the workpiece 102 thereby bringing substantially the entire outer circumference of the workpiece 102 into contact with the fluid jet 116.

In some embodiments, the drive system 520 can discontinuously rotate the workpiece 102. The drive motor 270, for example, can be a stepper motor or other type of motor suitable for controllably rotating (e.g., rotating in steps) the workpiece 102 about the axis of rotation 534.

Figure 15:
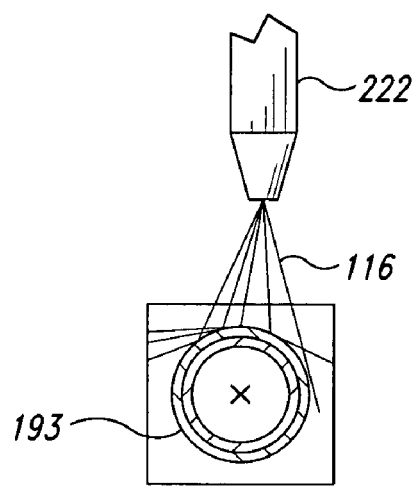
FIG. 15 is a cross-sectional view of the workpiece and mandrel disposed therethrough taken along a line 14-14 of FIG. 13, wherein the fluid jet is a fan jet processing the workpiece.

FIG. 15 shows the fluid jet 116 in the form of a fan jet that may be used in a similar manner as the fluid jet 116 of FIG. 14, except as further detailed below. The fan jet 116 of FIG. 15 can surface-finish the outer periphery 193 of the workpiece 102 in a relatively short amount of time and, in some embodiments, may provide a more even surface-finish than a surface-finish produced by a round fluid jet. Although the fan jet 116 is especially well suited for deburring, milling, and cutting, the fan jet 116 can also be used for cleaning or roughening the outer surface 193 of the workpiece 102. The illustrated fan jet 116 is oriented generally perpendicular to the longitudinal axis of the workpiece 102. However, the fan jet 116 can be at other orientations.

The delivery conduit 222 for producing the fan jet 116 can have various types of configurations. U.S. Pat. Nos. 5,512,318 and 6,019,298, which are both incorporated by reference in their entireties, disclose different types of nozzles and orifice designs suitable for producing fan jets. Other types of nozzles or tip designs can also be used to produce fan jets with the desired flow characteristics.

Figure 16:
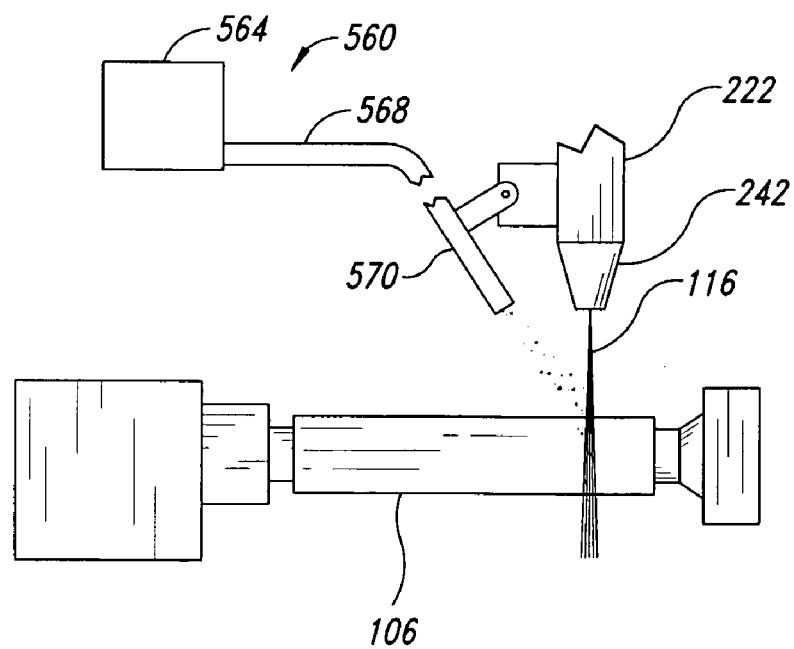
FIG. 16 is a side elevational view of a processing apparatus, in accordance with one illustrated embodiment.

The fan jet 116 of FIGS. 15 and 16 may or may not include any media. In some embodiments, for example, the fan jet 116 may include an entrained media (e.g., abrasives). In other embodiments, the fan jet 116 may be a water fan jet without any media.

FIG. 16 shows a media delivery system 560 for applying a media to the workpiece 102. The media delivery system 560 can include a media source 564, a delivery line 568, and an output 570. Media 572 from the media delivery system 560 may be delivered in proximity to the fluid jet 116. In some embodiments, the media 572 is delivered at the location of the intersection of the fan jet 116 and workpiece 102. The fan jet 116 thus carries the media 572 against the outer surface of the workpiece 102. In other embodiments, the media 572 is entrained with the fluid jet 116 at some point between the tip 242 and the workpiece 102. In other embodiments, the media 572 is applied to the workpiece 102 before interacting with the fluid jet 116. For example, the media 572 can be applied onto the workpiece 102 slightly ahead of the fluid jet 116 such that the fluid jet 116 passes over the applied media 572.

To maintain proper delivery of the media 572, the output 570 can be coupled to the delivery conduit 222. Various types of mounting arrangements can be used to mount the output 570 to the delivery conduit 222.

The media 572 and fluid jet 116 can be used to roughen the workpiece 102. In such embodiments, the media 572 can be an abrasive (e.g., aluminum oxide, garnet, sand, and the like). The system 560 can also be used for cleaning, polishing, or other performing surface-finishing processes.

FIG. 17 shows an apparatus 600 that is generally similar to the apparatus 500 of FIG. 10, except as further detailed below. The illustrated apparatus 600 includes a holder system 510 that generally aligns the workpiece 102 with the fluid jet 116 for surface processing a longitudinal section of the outer surface of the workpiece 102. The holder system 510 has a solid mandrel for minimizing or limiting off-axis movement of the workpiece 102 because of the tight tolerances needed to accurately process the workpiece 102.

The holder system 510 can be moved between the horizontal orientation of FIG. 10 and the vertical orientation of FIG. 17. The angle of incidence defined between the fluid jet 116 and the workpiece 102 can be selected based on the function of the fluid jet 116. To form cutouts, holes (e.g., vent holes), or other similar features, the workpiece 102 can be at various orientations with respect to the fluid jet 116.

The mandrel 524 of FIG. 17 has a tapered tip 603 to facilitate proper placement of the workpiece 611. If the workpiece 611 is a tubular workpiece, for example, the tapered tip 603 can be conveniently inserted into and advanced through a passageway of the workpiece 611. In this manner, the workpiece 611 can be easily slid over the mandrel 524. The illustrated tapered tip 603 is generally conical in shape. The holder 522 can have a complementary recess 615 for receiving and engaging the tapered tip 603. The tapered mandrel 524 of FIG. 17 can be used with the holder systems described in connection with FIGS. 10-16.

Figure 18:
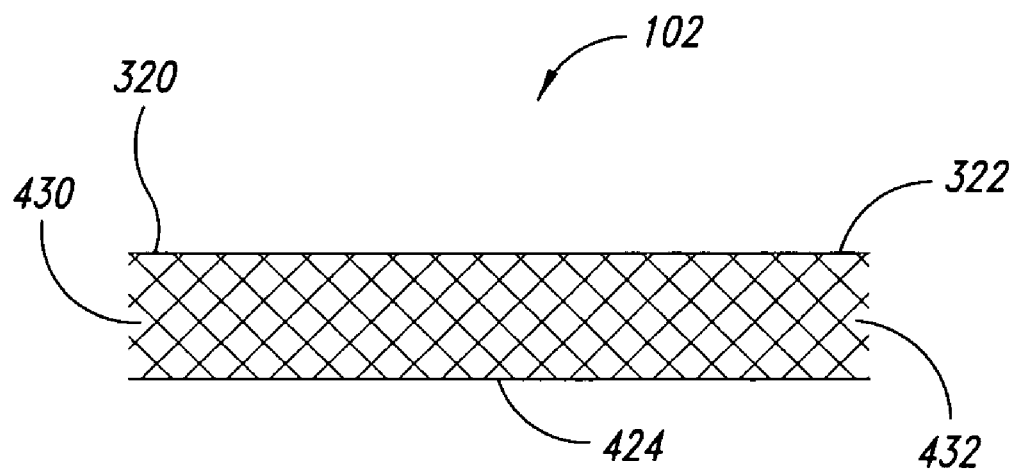
FIG. 18 is a side elevational view of a workpiece, in accordance with one illustrated embodiment.
Figure 19:
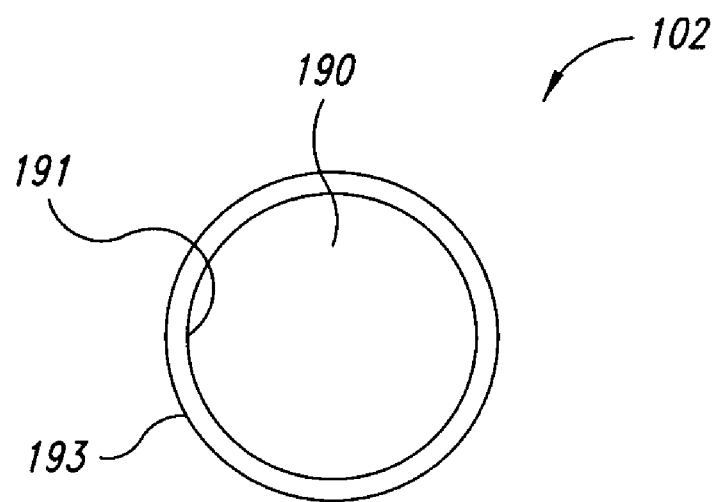
FIG. 19 is a top plan view of the workpiece of FIG. 18.

As noted above, various types of workpieces can be used with the processing apparatuses described above. FIGS. 18 and 19 show the tubular workpiece 102 suitable for use in the processing apparatus 100. The illustrated workpiece 102 includes the first end 320, second end 322, and a tubular main body 424 extending between the first and second ends 320, 322. The central lumen 190 extends between a first opening 430 at the first end 320 and a second opening 432 at the second end 322.

The tubular main body 424 has the inner surface 191 defining the central lumen 190 and an opposing outer surface 193 for engaging holder 124. Depending on the manufacturing process used to form the main body 424, the inner surface 191 and/or outer surface 193 may have burrs, protuberances, or other unwanted features extending radially inward or outward from the sidewall 376 of the main body 424.

The fluid jet 116 can be sized to fit within the relatively narrow lumen 109. In some embodiments, the jet 116 is sized to fit within the lumen 109 having a diameter equal to or less than about 0.05 inch (1.27 mm). The length of the tubular workpiece 102 to inner diameter ratio can be equal to or greater than about 7, 8, 10, 12, 14, and ranges encompassing such ratios. In some embodiments, the ratio of the length of the tubular workpiece 102 to inner diameter is about 10. In some embodiments, the tubular member 102 has an inner diameter in the range of about 0.01 inch (0.25) to about 0.03 inch (0.76 mm) and an axial length in the range of about 1 inch (25 mm) to about 10 inches (254 mm).

The workpiece 102 can be in the form of a luminal prosthesis for deployment in a body lumen of a subject. For example, the workpiece 102 can be a stent adapted to maintain luminal patency. The term "stent" generally refers, without limitation, to a generally tubular body dimensioned for placement within body lumens in the vascular system, respiratory system, digestive system, and other known locations suitable for stent implantation. The tubular stent may have a generally circular cross-section, elliptical cross-section, polygonal cross-section (including rounded polygonal), and other cross-sections suitable for defining or engaging a lumen.

The dimensions of the stent can be selected based on the implantation site. Exemplary stents include, without limitation, vascular stents (e.g., arterial stents), biliary stents, tracheal stents, and bronchial stents. In some embodiments, the lumen 109 of the stent 102 has diameter equal to or less than about 0.4 inch (10 mm). Most or a substantial portion of the fluid jet can be delivered into the lumen 109. In some embodiments, the lumen 109 of the stent 102 has diameter equal to or less than about 0.31 inch (8 mm), 0.24 inch (6 mm), or 0.16 inch (4 mm), or ranges encompassing such diameters. Tracheal stents can have lumens 109 with diameters less than or equal to about 0.4 inch (10 mm), 0.44 inch (11 mm), 0.47 inch (12 mm), 0.5 inch (13 mm), 0.55 inch (14 mm), or 0.6 inch (15 mm).

The stents, in some embodiments, may be expanded to form an open lattice structure (illustrated in FIG. 18). The processing apparatuses 100, 500, 600 can advantageously produce various types of surface-finishes to improve the performance of the stent 102. One type of surface-finish is an extremely smooth inner surface 191 in which fluid can flow easily along during use.

The surface roughness of the stent 102 can be reduced to reduce or limit the amount of material buildup attributable to the presence of the stent 102. If the stent 102 is placed in a vascular lumen, blood can flow smoothly over the stent 102 with thrombus accumulation kept at or below a desired level. In addition to removing unwanted material (including structural and non-structural materials, such as burrs), the fluid jet surfacing process can remove contaminates (e.g., contaminants often deposited during normal stent machining and handling) that may otherwise remain attached to stent, even if a subsequent cleaning process is performed.

In some embodiments, the workpiece 102 is used to produce a stent graft. A stent graft can include a frame (e.g., the illustrated stent 102 or other scaffold structure) that carries a covering, such as a membrane, liner, or other permeable or impermeable layer for covering at least portion of the frame. This frame can be processed with the fluid jets described herein, and the covering can then be coupled to either the inner surface or outer surface of the frame. In other embodiments, the frame is embedded in the covering. The stent graft can direct fluid flow (e.g., to block blood flow into aneurysms or other damaged areas), protect vessels walls, and/or reinforce vessel walls.

Various techniques can be used to form the covering on the illustrated stent 102 in order to form a stent graft. Dip coating, spray coating (e.g., ultrasonic spray coating, electrostatic spray-coating, etc.), deposition processes, and other processes can form a covering. In other embodiments, extruded sheets or profiles are attached to the stent 102.

Surface roughness can be chosen based on the subsequently applied materials. To promote surface adhesion, the surface roughness of the stent 102 can be increased to increase the stent's surface area to which the applied material can bond. Such roughened stents 102 are especially well suited for coating with medicaments or other coating materials suitable for use in a subject. A smooth exterior surface of the stent 102 can be used to limit or prevent damage to applied coverings.

If material is applied to the stent 102 by a dipping process, the apparatuses 100, 500, 600 can remove burrs, protuberances, or other surface irregularities that may collect and lead to the accumulation the coating material, such as biocompatible polymers. The localized material buildup may induce the formation of thrombus, and may also result in non-uniform mechanical properties of the stent. The non-uniform mechanical properties can impair proper functioning of the stent 102. The processing apparatuses 100, 500, 600 can advantageously surface-finish the stent 102 to remove any features that may undesirably impact the manufacturing process or stent performance in situ.

The surface-finishing process can produce a stent 102 with generally unidirectional lay, which generally refers to the predominant direction of the surface texture. For example, the fluid jet 116 of FIG. 1 forms unidirectional texture marks (e.g., striations) extending longitudinally along the inner surface 191 of the workpiece 102. Advantageously, these texture marks can be generally aligned with fluid flow through the central lumen 190 when the stent 102 in positioned in situ, thus allowing fluid to flow easily along its inner surface 191 to reduce hemodynamic disturbances, such as blood flow turbulence. Such a stent may help reduce the occurrence of stent thrombosis and other thrombosis related events.

Circumferential texture marks can be formed with the apparatus 500 of FIG. 10. These marks can increase frictional interaction between the stent 102 and the lumen wall in which it contacts to minimize or reduce stent migration. The orientation, depth, and width of the marks can be selected based on the desired interaction with the tissue in which the stent contacts.

If a stent having protrusions is used to form a stent graft, the protrusions can puncture and tear the covering forming holes in which fluid can pass through. The processing apparatuses 100, 500, 600 can remove such protrusions, or sufficiently round or blunt the protrusions, to prevent unwanted damage to the covering. This ensures proper stent graft functioning even over extended periods of times under various loading conditions (e.g., static or dynamic loading).

With continued reference to FIG. 18, the luminal prosthesis 102 can be self-expanding or expanded using a secondary device, such as an inflatable balloon. In self-expanding embodiments, the luminal prosthesis 102 can be formed, in whole or in part, of a shape memory material. The shape memory material may include, for example, a shape memory alloy (e.g., nitinol), a shape memory polymer, ferromagnetic material, combinations thereof, or other material(s). These materials can be transformed from a first preset configuration to a second preset configuration when activated (e.g., thermally activated). Thermal activation can be achieved via a subject's body heat, an external energy source (e.g., an ultrasound energy source), internal heating elements, and the like. Because the fluid jet 116 flows at relatively high flow rates, the surface-finishing can be performed without significantly altering the overall characteristics of the shape memory material. Even though the surface-finishing process may result in very localized heating of the prosthesis, the localized heating may not noticeably alter the overall physical properties of the prosthesis 102.

Of course, other types of workpieces can also be processed with the apparatuses disclosed herein. One of ordinary skill in the art can modify the apparatus 100, 500, 600 based on the material type, desired surface-finish, workpiece configuration, and end use of the workpiece.

All of the above U.S. patents, U.S. patent application publications, U.S. patent applications, foreign patents, foreign patent applications and non-patent publications referred to in this specification and/or listed in the Application Data Sheet, U.S. Pat. Nos. 6,000,308 and 5,512,318 are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of processing a workpiece, the method comprising:
   positioning a workpiece in a holder, the workpiece having an inner surface defining a central lumen;
   producing a fluid jet using fluid at a pressure of at least 10,000 psi;
   delivering the fluid jet through the central lumen of the workpiece in a first direction relative to the central lumen while the workpiece is in the holder;
   passing the fluid jet through the central lumen of the workpiece for a selected period of time such that the fluid jet removes a desired amount of material from the workpiece; and
   delivering the fluid jet through the central lumen of the workpiece in a second direction relative to the central lumen to remove material from the workpiece, the second direction being substantially opposite to the first direction.

2. The method of claim 1, further comprising:
after removing the desired amount of material and prior to delivering the fluid jet in the second direction, repositioning the workpiece in the holder.

3. The method of claim 1, further comprising:
substantially reducing an average surface roughness of a section of the inner surface.

4. The method of claim 1, further comprising:
radially moving the fluid jet within the central lumen of the workpiece.

5. The method of claim 1, further comprising:
rotating the workpiece about an axis of rotation while the fluid jet contacts an inner surface of the lumen.

6. The method of claim 5 wherein the fluid jet is radially offset from an axis of rotation defined by the holder.

7. The method of claim 1, further comprising:
mixing a first media with a pressurized fluid within a mixing chamber to produce the fluid jet that removes the desired amount of material from the workpiece;
flushing the mixture of the first media and pressurized fluid from the mixing chamber before mixing a second media with additional pressurized fluid in the mixing chamber to produce a second fluid jet; and
delivering the second fluid jet through the central lumen of the member.

8. The method of claim 1, further comprising:
removing fluid from the central lumen of the workpiece via an output line coupled to the holder.

9. The method of claim 8, further comprising:
operating a pressurization device in communication with the output line to provide a vacuum to the output line.

10. The method of claim 1 wherein the fluid jet is an abrasive fluid jet.

11. The method of claim 10, further comprising mixing abrasive and fluid to produce the abrasive fluid jet.

12. The method of claim 1 wherein producing the fluid jet comprises:
delivering the fluid through an orifice to form the fluid jet; and
delivering the fluid jet out of a delivery conduit towards the tubular workpiece.

13. The method of claim 1, further comprising:
pressurizing the fluid to at least 10,000 psi using a pressure fluid source fluidically coupled to a nozzle system configured to produce the fluid jet; and
delivering the pressurized fluid to the nozzle system.

14. The method of claim 1, further comprising:
positioning an outlet of a nozzle system outside of the central lumen such that the fluid jet travels out of the outlet towards the central lumen.

15. The method of claim 1, further comprising:
eroding the inner surface of the tubular workpiece using the fluid jet to polish the inner surface.

16. The method of claim 1, further comprising:
positioning the nozzle relative to the workpiece such that the fluid jet flows along a first direction path that is substantially parallel to a longitudinal axis of the central lumen when the fluid jet flows in the first direction; and
positioning the nozzle relative to the workpiece such that the fluid jet flows along a second direction path that is substantially parallel to the longitudinal axis of the central lumen when the fluid jet flows in the second direction.

17. The method of claim 1, further comprising:
positioning a nozzle outside of the central lumen of the workpiece while delivering the fluid jet in the first direction; and
positioning the nozzle outside of the central lumen of the workpiece while delivering the fluid jet in the second direction.

18. A method of processing a workpiece, the method comprising:
delivering a fluid jet from an end of a nozzle positioned outside of the workpiece towards an outer surface of the workpiece;
delivering media from a media nozzle of a media delivery system positioned outside of the workpiece such that the media outside of the workpiece moves towards the fluid jet to bring the media into contact with the fluid jet located outside of the workpiece;
moving the workpiece with respect to the fluid jet; and
carrying the media against the outer surface of the workpiece with the fluid jet until forming a desired surface finish while moving the workpiece.

19. The method of claim 18, further comprising:
combining the media in the fluid jet to form an abrasive fluid jet flowing towards the workpiece.

20. The method of claim 18, further comprising:
delivering the media towards a location of intersection in which the fluid jet contacts the workpiece such that the media and fluid jet are combined at least proximate the workpiece.

21. The method of claim 18, further comprising:
applying media to the workpiece; and
after applying the media, contacting the applied media and the workpiece with the fluid jet.

22. The method of claim 18 wherein delivering the media comprises directing a flow of the media from an output of the media delivery system towards the fluid jet while the output of the media delivery system is spaced apart from the nozzle and the fluid jet.

23. The method of claim 18 wherein delivering the media comprises delivering the media towards a portion of the fluid jet striking the tubular workpiece.

24. The method of claim 18, further comprising:
mixing the media and fluid of the fluid jet at a location proximate to the workpiece.

25. The method of claim 18, further comprising:
mixing the media and the fluid of the fluid jet at a location outside of the nozzle.

26. The method of claim 18, further comprising:
eroding a surface of the tubular workpiece using the fluid jet to polish the surface of the tubular workpiece.

27. A method of processing a tubular workpiece having a longitudinal length, the method comprising:
producing a fluid jet using fluid at a pressure of at least 10,000 psi;
delivering the fluid jet from a nozzle positioned relative to the tubular workpiece such that the fluid jet removes material from the tubular workpiece while the fluid jet extends along at least most of the longitudinal length of the tubular workpiece; and
positioning the fluid jet along a fluid path that is substantially parallel to a longitudinal axis of the tubular workpiece while removing the material from the tubular workpiece using the fluid jet.

* * * * *